(12) United States Patent
Irazoqui et al.

(10) Patent No.: US 12,161,877 B2
(45) Date of Patent: *Dec. 10, 2024

(54) MULTI-COIL WIRELESS POWER TRANSFER ASSEMBLY FOR WIRELESS GLAUCOMA THERAPY

(71) Applicant: Purdue Research Foundation, West Lafayette, IN (US)

(72) Inventors: Pedro P. Irazoqui, West Lafayette, IN (US); Gabriel Simon, West Lafayette, IN (US); Gabriel O. Albors, West Lafayette, IN (US); Jack Williams, Lafayette, IN (US); Quan Yuan, West Lafayette, IN (US); Zhi Wang, West Lafayette, IN (US); Curtis Slaubaugh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/084,070

(22) Filed: Dec. 19, 2022

(65) Prior Publication Data

US 2023/0119048 A1   Apr. 20, 2023

Related U.S. Application Data

(63) Continuation of application No. 16/636,273, filed as application No. PCT/US2018/045430 on Aug. 6, 2018, now Pat. No. 11,529,528.
(Continued)

(51) Int. Cl.
*A61N 1/36* (2006.01)
*A61N 1/40* (2006.01)
(Continued)

(52) U.S. Cl.
CPC .......... *A61N 1/40* (2013.01); *A61N 1/36046* (2013.01); *A61B 3/16* (2013.01); *A61F 9/00781* (2013.01)

(58) Field of Classification Search
CPC ........ A61N 1/40; A61N 1/36046; A61B 3/16; A61F 9/00781
See application file for complete search history.

(56) References Cited

U.S. PATENT DOCUMENTS

| 4,271,841 A | 6/1981 | Friedman |
| 4,603,697 A | 8/1986 | Kamerling |

(Continued)

FOREIGN PATENT DOCUMENTS

| CA | 2856314 | 6/2013 |
| WO | WO 2005072294 | 8/2005 |

(Continued)

OTHER PUBLICATIONS

Ahmed [online], "Addendum viii," Nov. 1993, [retrieved on Nov. 6, 2018], retrieved from: URL <https://www.accessdata.fda.gov/cdrh_docs/pdf/K925636.pdf>, 7 pages.
(Continued)

*Primary Examiner* — Catherine M Voorhees
(74) *Attorney, Agent, or Firm* — Fish & Richardson P.C.

(57) ABSTRACT

Systems and methods for wireless stimulation of biological tissue (e.g. nerves, muscle tissue, etc.) and, in one exemplary implementation, to therapy for glaucoma based on the wireless administration of energy to the eye of a mammalian subject (e.g. human, rodent, etc.) to reduce an elevated intraocular pressure (IOP) involving the use of a multi-coil wireless power transfer assembly. The multi-coil wireless power transfer assembly may be used alone or in combination-
(Continued)

tion with a stimulation coil that can be implanted in the eye of a mammalian subject or within a contact lens worn by a mammalian subject.

21 Claims, 20 Drawing Sheets

Related U.S. Application Data

(60) Provisional application No. 62/541,218, filed on Aug. 4, 2017.

(51) Int. Cl.
  *A61B 3/16* (2006.01)
  *A61F 9/007* (2006.01)

(56) References Cited

U.S. PATENT DOCUMENTS

| | | | |
|---|---|---|---|
| 4,614,193 A | 9/1986 | Liss | |
| 6,123,668 A | 9/2000 | Abreu | |
| 6,238,333 B1* | 5/2001 | Loos | A61N 2/02 977/950 |
| 6,443,893 B1 | 9/2002 | Schnakenberg | |
| 7,282,046 B2 | 10/2007 | Simon | |
| 8,029,431 B2* | 10/2011 | Tononi | A61M 21/02 600/9 |
| 8,128,588 B2 | 3/2012 | Coroneo | |
| 8,267,882 B2 | 9/2012 | Euteneuer et al. | |
| 8,415,364 B2 | 4/2013 | Epstein et al. | |
| 8,419,673 B2 | 4/2013 | Rickard | |
| 10,232,139 B1* | 3/2019 | Hang | A61M 21/00 |
| 11,191,961 B2* | 12/2021 | Irazoqui | A61N 2/02 |
| 11,191,962 B2 | 12/2021 | Irazoqui et al. | |
| 11,903,880 B2* | 2/2024 | Oduncu | A61F 9/02 |
| 2002/0013545 A1 | 1/2002 | Soltanpour et al. | |
| 2006/0224215 A1* | 10/2006 | Pattern | A61N 1/40 607/62 |
| 2007/0027537 A1 | 2/2007 | Castillejos | |
| 2007/0260107 A1* | 11/2007 | Mishelevich | A61N 2/004 600/14 |
| 2007/0282405 A1 | 12/2007 | Wong et al. | |
| 2009/0076367 A1* | 3/2009 | Sit | A61B 3/16 600/398 |
| 2010/0110368 A1* | 5/2010 | Chaum | G02C 11/10 351/158 |
| 2011/0022118 A1* | 1/2011 | Rickard | A61N 1/36046 607/53 |
| 2011/0238133 A1* | 9/2011 | Gross | A61N 1/205 607/53 |
| 2013/0006326 A1* | 1/2013 | Ackermann | A61N 1/3606 607/53 |
| 2013/0030415 A1 | 1/2013 | Britt | |
| 2013/0184554 A1* | 7/2013 | Elsheikh | A61B 3/16 600/398 |
| 2014/0031905 A1 | 1/2014 | Irazoqui et al. | |
| 2014/0213843 A1 | 7/2014 | Pilla et al. | |
| 2015/0257931 A1* | 9/2015 | Sanchez | A61F 9/00781 604/9 |
| 2017/0007834 A1 | 1/2017 | Irazoqui et al. | |
| 2017/0080207 A1* | 3/2017 | Perez | A61F 5/0003 |
| 2017/0105987 A1 | 4/2017 | Aberg et al. | |
| 2018/0161579 A1* | 6/2018 | Franke | A61B 5/1127 |
| 2018/0353766 A1 | 12/2018 | Casse et al. | |
| 2019/0009097 A1 | 1/2019 | Hartley et al. | |

FOREIGN PATENT DOCUMENTS

| | | |
|---|---|---|
| WO | WO 2009150688 | 12/2009 |
| WO | WO 2013063111 | 5/2013 |
| WO | WO 2015157725 | 10/2015 |
| WO | WO 2017223387 | 12/2017 |

OTHER PUBLICATIONS

Braendstrup [online], "Muscular bio stimulator (2nd version)," 2011, May, available: http://www.redcircuits.com/Page124.htm.
Chader, "Key needs and opportunities for treating glaucoma," Investigative Ophthalmology and Visual Science, May 2012, vol. 53, pp. 2456-2460.
Constable & Lim, Color Atlas of Ophthalmology. World Scientific Publishing Company, 1995.
DeLuca, "Draft guidance for industry and fda staff: Class ii special controls guidance document: Powered muscle stimulator for rehabilitation," CDRH, Apr. 5, 2010, 19 pages.
Detry-Morel, "Side effects of glaucoma medications," Bull. Soc. Belge Ophthal, 2006, vol. 299, pp. 27-40.
Dietlein, "The medical and surgical treatment of glaucoma," Dtsch Arztebl Int, 2009, vol. 116, pp. 597-606.
Extended European Search Report in EP Appln. No. 18840215.0, dated Apr. 8, 2020, 6 pages.
FDA [online], "Classify your medical device," 2012, Dec., available on or before Apr. 17, 2018, via Internet Archive: Wayback Machine URL: <https://web.archive.org/web/20180417153853/http://www.fda.gov/MedicalDevices/DeviceRegulationandGuidance/Overview/ClassifyYourDevice/>, [retrieved on Nov. 6, 2018], retrieved from: URL <http://www.fda.gov/MedicalDevices/DeviceRegulationandGuidance/Overview/ClassifyYourDevice/ >, 3 pages.
FDA [online], "Tomey dtl electrode," May 1997, [retrieved on Nov. 6, 2018], retrieved from: URL <https://www.accessdata.fda.gov/scripts/cdrh/cfdocs/cfPMN/pmn.cfm?ID=K961805>, 1 page.
FDA, "Guidance for industry and for fda reviewers/staff- guidance on 510(k) submissions for keratoprostheses," Mar. 1999, 11 pages.
Fechter, "Improvised 3-0 polypropylene plug for the glaucoma drainage tube during phacoemulsification," Ophthalmic. Surg. Lasers Imaging, Jan./Feb. 2008, vol. 39, pp. 86-87.
Fernandes et al, "Artificial vision through neuronal stimulation," Neuroscience Letters, Jun. 25, 2012, vol. 519, pp. 122-128.
Foster[online], "Specific questions related to glaucoma," available on or before Oct. 7, 2013, via Internet Archive: Wayback Machine URL : <https://web.archive.org/web/20131007014544/http://www.rcophth.ac.uk/page.asp?section=373&sectionTitle=Specific+Questions+Related+to+Glaucoma>, [retrieved on Nov. 6, 2018], 1 page.
G. R. Foundation [online], "Glaucoma facts and stats," Aug. 2013, [retrieved on Nov. 5, 2018], retrieved from: <http://www.glaucoma.org/glaucoma/glaucoma-facts-and-stats.php>, 3 pages.
G. Technologies [online], "Sd9 square pulse stimulator," available on or before Jul. 7, 2013, via iInternet Archive: Wayback Machine URL <https://web.archive.org/web/20130707155649/http://www.grasstechnologies.com/products/stimulators/stimsd9.html>, [retrieved Nov. 6, 2018], retrieved from: URL <http://www.grasstechnologies.com/products/stimulators/stimsd9.html>, 2 pages.
Ghosh et al., "Lens-solution interactions: Impact on biocompatibility," Presented at The 15th Symposium on the Material Science and Chemistry of Contact Lenses. Center for Devices and Radiological Health, FDA, Mar. 18, 2011, 43 pages.
Glaucoma Research Foundation [online], "Laser surgery," Aug. 25, 2017, [retrieved on Nov. 6, 2018], retrieved from: URL <http://www.glaucoma.org/treatment/laser-surgery.php>, 3 pages.
Greenwell and Spillman, "Use of medicated drops and oral tablets in glaucoma treatment," Curr Opin Ophthalmol., Apr. 1996, vol. 7, pp. 44-46.
International Search Report and Written Opinion in PCT Appln. No. PCT/US2018/045430, dated Oct. 3, 2018, 9 pages.
Janunts, "Optical remote sensing of intraocular pressure by an implantable nanostructured array," available: http://www.uniklinikum-saarland.de/en/facilities/departments and institutes/experimental ophthalmology/research/iop sensing/.
John M. Eisenberg Center for Clinical Decisions and Communications Science, "Comparisons of medical, laser, and incisional surgical treatments for open-angle glaucoma in adults," AHRQ, 2012, 4 pages.
Keenan, [online], "510(k) summary," Nov. 28, 2008, [retrieved on Nov. 6, 2018], retrieved from: URL <https://www.accessdata.fda.gov/cdrh_docs/pdf8/K082011.pdf>, 7 pages.

(56) References Cited

OTHER PUBLICATIONS

King et al, Clinical review: Glaucoma, BMJ, Jun. 15, 2013, vol. 346, pp. 29-33.
Kobayashi et al, "Accuracy of intraocular pressure by tono-pen xl over amniotic membrane patching in rabbits," American Journal of Ophthalmology, Apr. 2003, vol. 135, pp. 536-537.
Kok & Barton, "Uveitic glaucoma," Ophthalmol Clin North Am, vol. 15, pp. 375-387, 2002.
Lee et al, "Primary acute angle closure: long- term clinical outcomes over a 10 year period in the chinese population," Apr. 2014, vol. 34, pp. 165-169.
Leuven [online], Validation of retinal oximetry in glaucoma patients: a structural and functional correlation, Feb. 2013 [retrieved on Nov. 5, 2018], retrieved from: <http://www.clinicaltrials.gov/ct2/show/NCT01391247?term=glaucoma&rank=13>, 6 pages.
Lewinstein et al, "Antibacterial properties of aged dental cements evaluated by direct-contact and agar diffusion tests," Journal of Prosthetic Dentistry, Apr. 2005, vol. 93, pp. 364-371.
Lu et al, "Electrical stimulation with a penetrating optic nerve electrode array elicits visuotopic cortical responses in cats." J Neural Eng, Jun. 2013, vol. 10, pp. 1-11.
Lusby et al [online], "Glaucoma," Sep. 2011, [retrieved on Nov. 5, 2018], retrieved from: <http://www.nlm.nih.gov/medlineplus/ency/article/001620.htm>, 8 pages.
Managed Care Eye Institute [online], "Coats of the eye: Ciliary body," Jan. 2012, [retrieved on Nov. 5, 2018], retrieved from: <http://teaching.pharmacy.umn.edu/courses/eyeAP/Eye_Anatomy/CoatsoftheEye/CiliaryBody.htm>, 1 page.
Mayo Clinic Staff [online], "Glaucoma: Treatment and drugs," Oct. 2012, available: [retrieved on Nov. 5, 2018], retrieved from <: www.mayoclinic.com/health/glaucoma/DS00283/DSECTION=treatments-and-drugs>, 5 pages.
Moorthy, "Glaucoma associated with uveitis," Surv Ophthalmol, 1997, pp. 361-394.
Mountaintop Medical, "Advances in opthamology: Markets in the treatment of eye disorders and corrective vision," Jul. 2009.
Murgatroyd & Bembridge, "Intraocular pressure," Oxford Journal of Medicine, 2008, vol. 8, pp. 100-103.
Nesterov & Khadikova [online], "Effect of ciliary muscle electrical stimulation on ocular hydrodynamics and visual function in patients with glaucoma," Vestn Oftalmol., 1997, vol. 113, pp. 12-14 [English Abstract].
Optonol Ltd [online], "Summary of safety & effectiveness," Mar. 1, 2003, [retrieved on Nov. 6, 2018], retrieved from: URL <https://www.accessdata.fda.gov/cdrh_docs/pdf3/K030350.pdf>, 5 pages.
Optonol Ltd. [online], "510(k) summary," Mar. 2002, [retrieved on Nov. 6, 2018], retrieved from: URL <https://www.accessdata.fda.gov/cdrh_docs/pdf/K012852.pdf>, 7 pages.
Panarelli et al, "Scleral stula closure at the time of glaucoma drainage device tube repositioning: a novel technique," Arch Ophthalmol., Nov. 2012, vol. 130, pp. 1447-1451.
Pescosolido et al, "Role of dopaminergic receptors in glaucomatous disease modulation," Biomed. Res. Int., 2013, 5 pages.
Pham & Hu, "Cytotoxicity evaluation of multipurpose contact lens solutions using an in vitro test battery," CLAO Journal, Jan. 1999, vol. 25.
Porcari et al, "Effects of electrical muscle stimulation on body composition, muscle strength, and physical appearance," Journal of Strength and Conditioning Research, 2002, vol. 16, pp. 165-172.
Quigley & Vitale, "Models of open-angle glaucoma prevalence and incidence in the United States," Investigative Ophthalmology and Visual Science, Jan. 1997, vol. 38, pp. 83-91.
Shields, Shields textbook of glaucoma. Philadelphia, PA: Lippincott Williams & Wilkins, 2005.
Sjogren and Dahl, "Cytotoxicity of dental alloys, metals, and ceramics assessed by millipore filter, agar overlay, and mtt tests," Elsevier, Aug. 2000, vol. 84, pp. 229-236.
Sun et al, "Spatiotemporal properties of multipeaked electrically evoked potentials elicited by penetrative optic nerve stimulation in rabbits," Investigative Ophthalmology and Visual Science, Aug. 2010, vol. 52, pp. 146-154.
Texas Instruments, "Lm741 operational amplifier," Mar. 2013, 11 pages.
V. E. S. Center [online], "Ahmed valve glaucoma implant with adjunctive subconjunctival bevacizumab in refractory glaucoma," May 2010, available: http://www.clinicaltrials.gov/ct2/show/NCT01128699?term=glaucoma&rank=15>, 6 pages.
Valk, "Intraocular pressure-lowering effects of all commonly used glaucoma drugs: a meta-analysis of randomized clinical trials," Ophthalmology, 2005, vol. 112, pp. 1177-1185.
Wang et al, "Intervention of laser periphery iridectomy to posterior iris bowing in high myopic eyes," Chin. Med. J. (Engl)., Dec. 2012, vol. 125, pp. 4466-4469.
Wong & Graham, "Effect of repeat use and coating defects of gold foil electrodes on electroretinogram recording," Vision Research, 1995, vol. 35, pp. 2795-2799.
Extended European Search Report in EP Appln. No. 23214204.2, dated May 6, 2024, 6 pages.

* cited by examiner

MULTI-COIL WIRELESS POWER TRANSFER ASSEMBLY FOR WIRELESS GLAUCOMA THERAPY

CROSS-REFERENCE TO RELATED APPLICATIONS

This application is a continuation of U.S. application Ser. No. 16/636,273, filed on Feb. 3, 2020, which is a National Phase Application under 35 U.S.C. § 371 of International Application No. PCT/US2018/045430, filed on Aug. 6, 2018, which claims the benefit of U.S. Provisional Application No. 62/541,218, filed on Aug. 4, 2017. The contents of the aforementioned application are hereby incorporated by reference in their entirety.

BACKGROUND

1. Technical Field

The present disclosure relates generally to wireless stimulation of biological tissue (e.g. nerves, muscle tissue, etc.) and, in one exemplary implementation, to therapy for glaucoma based on the wireless administration of energy to the eye of a mammalian subject (e.g. human, rodent, etc.) to reduce an elevated intraocular pressure (IOP) involving the use of a multi-coil wireless power transfer assembly. The multi-coil wireless power transfer assembly may be used alone or in combination with a stimulation coil that can be implanted in the eye of a mammalian subject or within a contact lens worn by a mammalian subject.

2. Background Information

Glaucoma is currently the leading cause of blindness and continues to cause blindness in around 10% of even those patients who receive the most up to date treatment. The primary cause of glaucoma is an excess of intraocular pressure (IOP) which presses on and damages the optic nerve. In a normally functioning mammalian eye, fluid (namely, aqueous humor) is pumped into the anterior segment of the eye to, among other things, maintain a healthy IOP and provide nutrients to the structures in the anterior segment. The fluid is then drained out primarily through the drainage tissues at the junction of the cornea and iris in the region of the eye known as the limbus. In glaucoma, an elevated IOP results from an excess of aqueous humor which may be due to a combination of a) the ciliary body producing too much fluid (increased inflow) and/or b) too much resistance to aqueous humor drainage out of the eye (limited outflow) depending upon the type of glaucoma.

Glaucoma may take many forms. Open-angle glaucoma is where the aqueous humor does not drain as quickly due to abnormal resistance in the trabecular meshwork and Schlemm's canal pathway. The increase in IOP in open-angle glaucoma is usually a slow process and generally does not exhibit any symptoms. When vision starts to decrease, severe damage has already been done to the optic nerve. Closed-angle (sometimes referred to as "Angle-closure glaucoma") is where the aqueous humor does not drain from the eye because of a blockage or resistance in the trabecular network by the iris. This causes a sudden spike in the intraocular pressure and is considered an emergency. Congenital glaucoma is a birth defect caused by abnormal eye development. Secondary glaucoma is caused by external factors such as drugs, disease, or trauma. Open-Angle glaucoma is the most common form of glaucoma and has a clear genetic component. When considered in all forms, the populations of patients with glaucoma or high IOP (pre-glaucoma) are predicted to grow steadily due to, among other reasons, the demographic increase in the aging population.

Existing medical and surgical treatments attempt to reduce IOP to non-damaging levels by targeting either the drainage or production of aqueous humor, but with limited success. The two primary approaches include the use of eye-drops to regulate fluid flow and surgeries to open drainage channels in the eye. The pharmacological (eye-drop) methods for reducing IOP in glaucoma and ocular hypertensive patients provide only acute relief of symptoms for the chronic disease. The surgical approaches have largely focused on implanting a stent or similar structure to wick or facilitate the drainage of aqueous humor. Laser surgical approaches achieve a similar effect as stents by creating or increasing openings in the drainage region of the eye. Bleb surgeries create an opening out of the anterior chamber to facilitate drainage. Such surgical approaches have enjoyed limited clinical success for a host of reasons, including the increased risk of infection due to the bacterial pathway that exists by virtue of the physical drainage element (e.g. bleb) extending outside the eye during use. The same infection risk is present for the prior art efforts involving the use of electrical stimulation of the eye to reduce IOP, which typically include hard-wired electrodes with leads extending from the eye during use.

SUMMARY

There is a need to develop a method to chronically reduce IOP of patients with glaucoma or ocular hypertension to a safe level without causing unacceptable side effects.

The details of one or more embodiments of the subject matter described herein are set forth in the accompanying drawings and the description below. Other features, aspects, and advantages of the invention will become apparent from the description, the drawings, and the claims.

In some implementations, a system for wirelessly reducing elevated intraocular pressure in an eye of a mammalian subject includes a coil constructed from an elongated conductor formed into a plurality of windings. Said coil is adapted to be positioned in proximity to an eye of a mammalian subject. The system also includes a signal generator in electrical communication with said coil. Said signal generator is configured to generate a signal to produce an electromagnetic field transmitted wirelessly from said coil to said eye of said mammalian subject in a therapeutically effective amount to reduce an elevated intraocular pressure within said eye of said mammalian subject.

In some implementations, a device for reducing elevated intraocular pressure in an eye of a mammalian subject includes a stimulation electrode assembly adapted to be positioned at least one of on, within or near said eye of said mammalian subject. Said passive stimulation electrode assembly is adapted to deliver a stimulation signal to at least one intraocular structure in a therapeutically effective amount to reduce said elevated intraocular pressure within a mammalian eye by (i) decreasing aqueous humor inflow into an anterior segment of said eye, and (ii) increasing aqueous humor outflow from said anterior segment of said eye.

In some implementations, a method of wirelessly reducing elevated intraocular pressure in an eye of a mammalian subject includes transmitting an electromagnetic field wirelessly from a coil to an eye of a mammalian subject, the electromagnetic field delivered in an amount therapeutically effective to reduce an elevated intraocular pressure within said eye. Said coil can be constructed from an elongated conductor formed into a plurality of windings.

In some implementations, a method of reducing elevated intraocular pressure in an eye of a mammalian subject includes transmitting an electromagnetic field to a stimulation electrode assembly positioned near an eye of a mammalian subject. The stimulation electrode assembly is adapted to stimulate at least one intraocular structure to reduce an elevated intraocular pressure within said mammalian eye by (i) decreasing aqueous humor inflow into an anterior segment of said eye, and (ii) increasing aqueous humor outflow from said anterior segment of said eye.

DRAWING DESCRIPTIONS

Like references, numbers and designations in the various drawings indicate like elements.

DETAILED DESCRIPTION

The methods and devices described in the present disclosure enables the wireless administration of energy to an eye of a mammalian subject for the purpose of reducing elevated intraocular pressure (IOP) for those experiencing glaucoma or pre-glaucoma ocular hypertension. This reduction in IOP is based on the delivery of time-varying electromagnetic fields to the eye in a therapeutically effective amount sufficient to (1) decrease the inflow of aqueous humor into the anterior segment of the eye (so-called "fluid inflow decrease") and/or (2) increase the outflow of aqueous humor from the anterior segment of the eye (so-called "fluid outflow increase"). As used herein, the "anterior segment" of the eye is the front third of the eye that includes the structures in front of the vitreous humor: namely the cornea, the iris, the ciliary body, and the intraocular lens. There are two fluid-filled spaces within the anterior segment of the eye: the anterior chamber and the posterior chamber. The anterior chamber of the anterior segment exists between the posterior surface of the cornea (i.e. the corneal epithelium) and the iris. The posterior chamber of the anterior segment extends between the iris and the suspensory ligament of the lens. Aqueous humor fills the spaces of the anterior chamber and posterior chamber to, among other things, provide nutrients to the surrounding structures. The wireless administration of energy to reduce IOP may take multiple forms, as will be described below.

Figure 1:
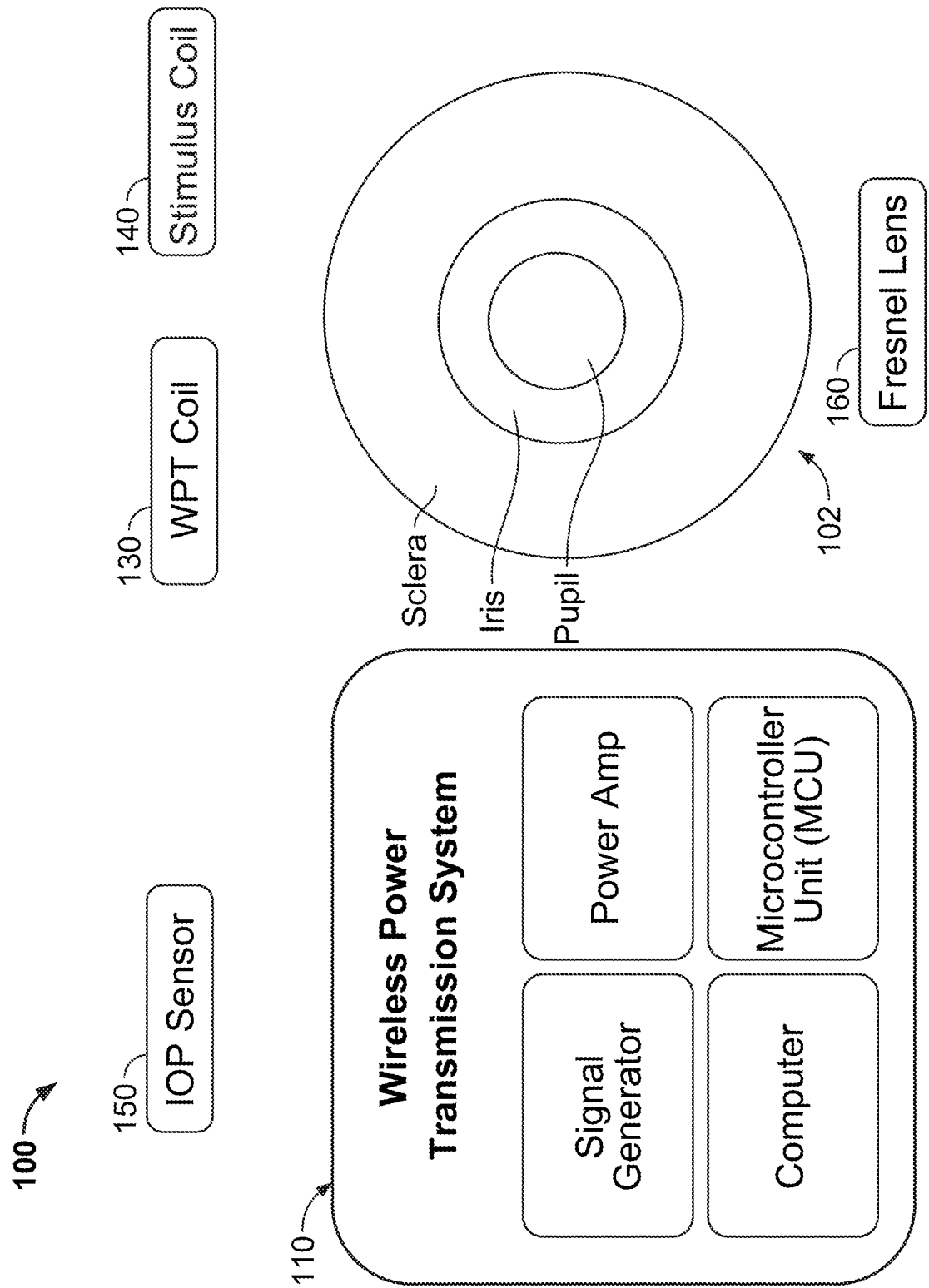
FIG. 1 shows a diagram of a wireless glaucoma therapy system, including a wireless power transfer (WPT) system, a WPT coil, a Stimulus Coil, according to an exemplary embodiment.

FIG. 1 is a block diagram of a wireless glaucoma therapy system 100 for delivering a time-varying electromagnetic field to an eye 102 of a mammalian subject according to the principles and techniques disclosed herein. To do so, the wireless glaucoma therapy system 100 includes a wireless power transfer (WPT) system 110 having suitable control and driving circuitry (e.g. signal generator, power amp, microcontroller unit, computer) for generating a time-varying electromagnetic field from a WPT coil 130 positioned and configured to deliver the time-varying electromagnetic field to the eye 102, either directly or alternatively via stimulus coil 140. The WPT system 110 and the WPT coil 130 may be communicatively linked in any number of suitable manners, including a hard-wired connection (e.g. cable) as well as via wireless communication technologies.

As will be described below, the WPT coil 130 may be positioned near the eye 102 in any number of suitable manners, including but not limited to devices to enable the administration of wireless glaucoma therapy during normal activities of daily living (e.g. WPT coil 130 on eye-glasses), devices to enable the administration of wireless glaucoma therapy in a clinical setting (e.g. WPT coil 130 on an optical frame used by ophthalmologists and/or optometrists), and devices to enable the administration of wireless glaucoma therapy while the subject is sleeping (e.g. WPT 130 as part of a sleep mask, pillow, etc.). In each case, the WPT coil 130 delivers the time-varying electromagnetic field to the eye 102 in a therapeutically effective amount to reduce the IOP within the eye 102 by decreasing the inflow and/or increasing the outflow of aqueous humor into and out of, respectively, the anterior segment of the eye 102.

In another embodiment, the wireless glaucoma therapy system 100 may include a stimulus coil 140 disposed on or within the eye 102. The stimulus coil 140 is configured to receive the electromagnetic field generated by the WPT coil 130 and transmit that energy directly into the eye 102. The physical location of the stimulus coil 140 on or within the eye 102 provides a higher level of energy transmission into the eye 102, which can result in IOP reduction in a shorter time period or to a greater extent than that accomplished by the WPT system 110 and WPT coil 130 alone. The stimulus coil 140 may be disposed and configured in any number of suitable manners, including (but not necessarily limited to) on or within a contact lens and/or surgically implanted into any suitable area within the eye 102 (e.g., intraocular lens (IOL), sub-conjunctival region, etc.).

In a still further embodiment, the wireless glaucoma therapy system 100 may include a wireless IOP sensor 150 capable of monitoring the intraocular pressure (IOP) within the eye 102. The wireless IOP sensor 150 may be implantable within the eye 102 and communicatively linked with the WPT system 110 to regulate or modify the delivery of therapy in a closed-loop manner based on the values of the monitored IOP. The closed-loop control of the WPT system 110 (including WPT coil 130 and optionally the stimulus coil 140) may be accomplished in any suitable manner, including but not limited to the use of executable software on the computer and/or an "app" on a smartphone, tablet, etc., to modify the delivery of the wireless glaucoma therapy based on the measured IOP in the eye 102.

In yet another embodiment, a Fresnel lens 160 may be employed (used separately or as part of the glaucoma therapy system 100) to focus incoming light rays onto the retina of the eye 102 for the purpose of vision correction. The Fresnel lens 160 may be constructed with a series of metallic traces in order to establish a given optical power to achieve vision correction, namely, by focusing light passing through the Fresnel lens 160 on the retina of the eye 102. The metallic traces of the Fresnel lens 160 may also be capable of receiving the time-varying electromagnetic fields and delivering that energy to the eye for the purpose of glaucoma therapy, especially if the Fresnel lens 160 is electrically coupled to a stimulus coil 140. The Fresnel lens 160 may be employed with the WPT system 110 (including WPT coil 130) in order to deliver glaucoma therapy in addition to vision correction.

Figure 2:
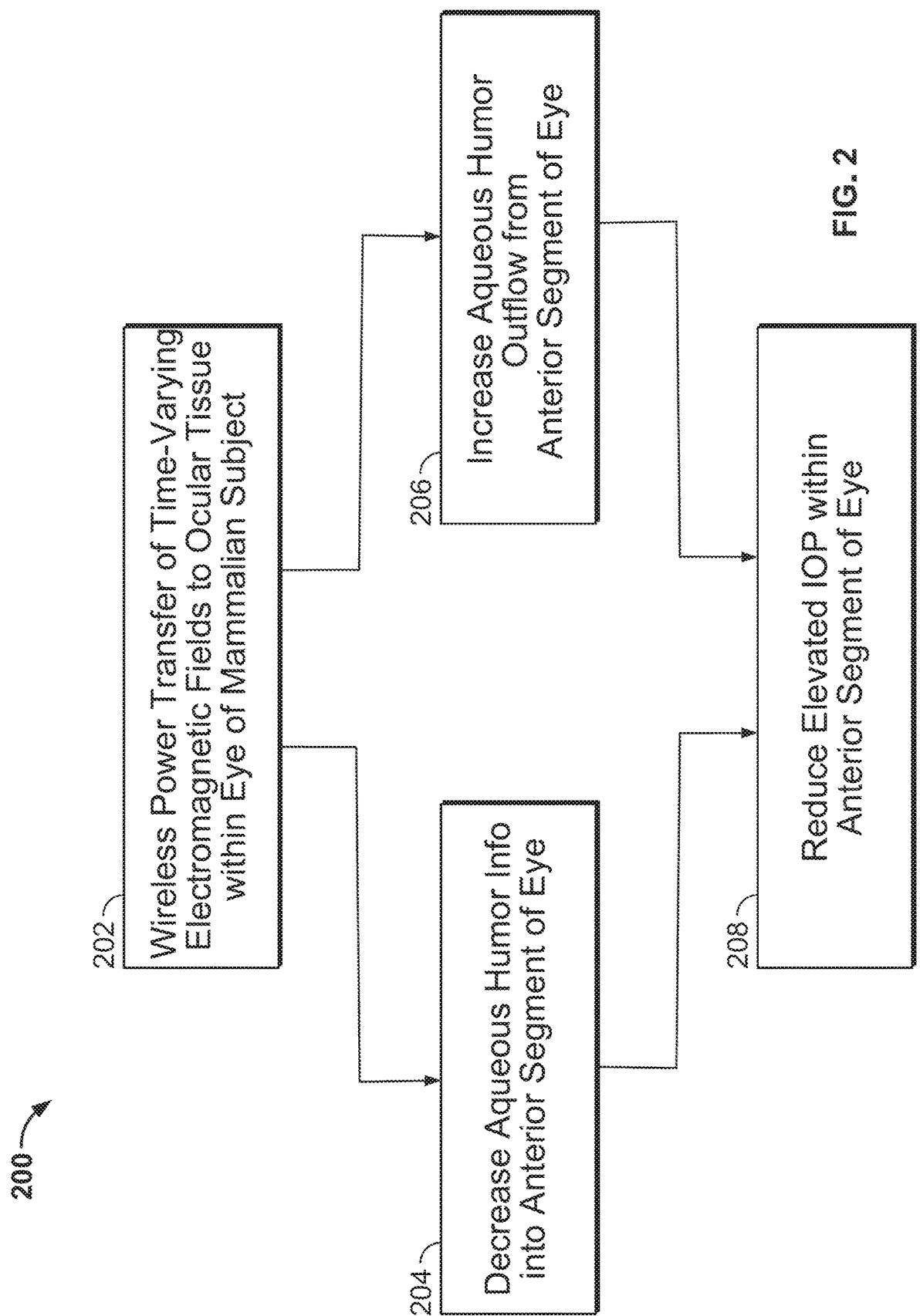
FIG. 2 shows a methodology of the wireless glaucoma therapy system of FIG. 1, according to an exemplary embodiment.

FIG. 2 shows a methodology 200 of the wireless glaucoma therapy system (e.g., system 100 shown in FIG. 1). Step 202 involves wirelessly transmitting power in the form of time-varying electromagnetic fields to ocular tissue with an eye of a mammalian subject (e.g., eye 102 shown in FIG. 1). Depending upon the manner of wireless power transfer, the wireless transmission of power (step 202) will result in a decrease in aqueous humor inflow into the anterior segment of the eye (step 204) and/or an increase in aqueous humor outflow from the anterior segment of the eye (step 206). More specifically, the wireless transmission of energy via WPT coil (e.g., WPT coil 130 of FIG. 1), with or without a stimulus coil (e.g., stimulus coil 140 of FIG. 1), may provide both a decrease in the aqueous humor into the anterior segment of the eye (step 204) and an increase in the aqueous humor outflow from the anterior chamber of the eye (e.g., eye 102), thus reducing an elevated IOP within the anterior segment of the eye (208).

Figure 3:
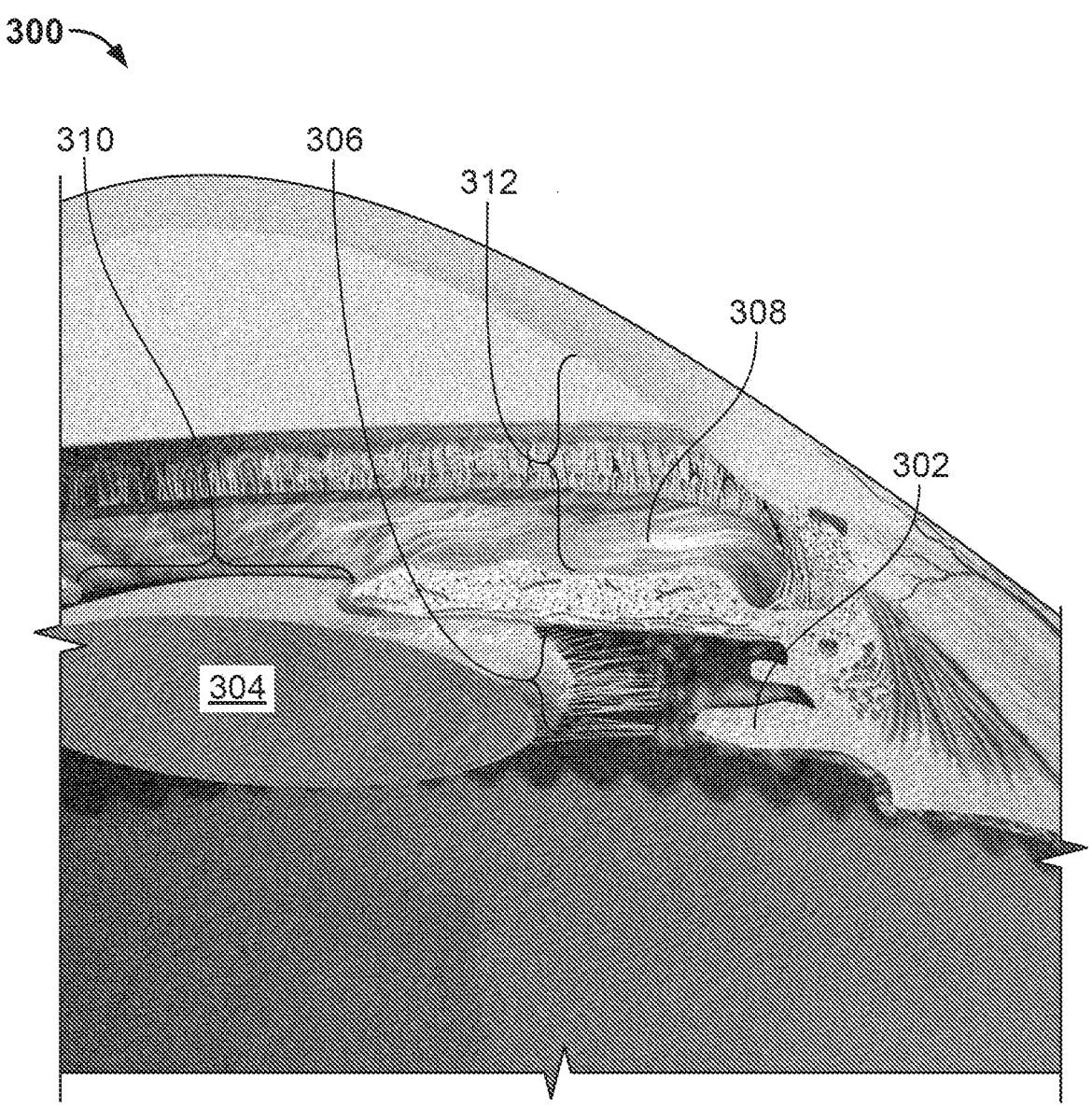
FIG. 3 shows a diagram of the anatomy of an eye of a mammalian subject, according to an exemplary embodiment.

FIG. 3 shows a diagram of the anatomy of an eye 300 of a mammalian subject, specifically in this figure, a human. Within the eye 300, the ciliary body 302 includes a smooth-muscle tissue called the ciliary muscle, which has two different orientations of muscle (circular and longitudinal) with separate functions. The circular muscle tissue of the ciliary body 302 controls the shape of the lens 304 in the eye 300, which changes the focus of the eye 300 so that the image will be clear on the back of the retina. The longitudinal muscle tissue of the ciliary body 302 controls the configuration of the trabecular meshwork. The aqueous humor is secreted by the ciliary body 302.

Aqueous humor is secreted into the posterior chamber 306 of the anterior segment of the eye 300 between the iris 308 and lens 304. It washes over the lens 304 and then moves through the pupil 310 into the anterior chamber 312 of the anterior segment. Ultimately, much of the aqueous humor leaves the eye 300 through two primary pathways, namely a pathway through as least part of the Canal of Schlemm and an uveoscleral pathway through at least part of the ciliary body and choroid. Aqueous humor production, flow and drainage are important for nourishing the front of the eye 300, removing metabolites and normal vision.

In a patient with glaucoma, the aqueous humor builds up in the eye 300. This can be due to the blocking or a slowing of the drainage of the aqueous humor in the trabecular meshwork. As the excess fluid builds in the eye 300, it increases the intraocular pressure. As this pressure increases, it causes the optic nerve to get damaged. If left untreated, the pressure does so much damage to the optic nerve that it can eventually lead to blindness.

Figure 4:
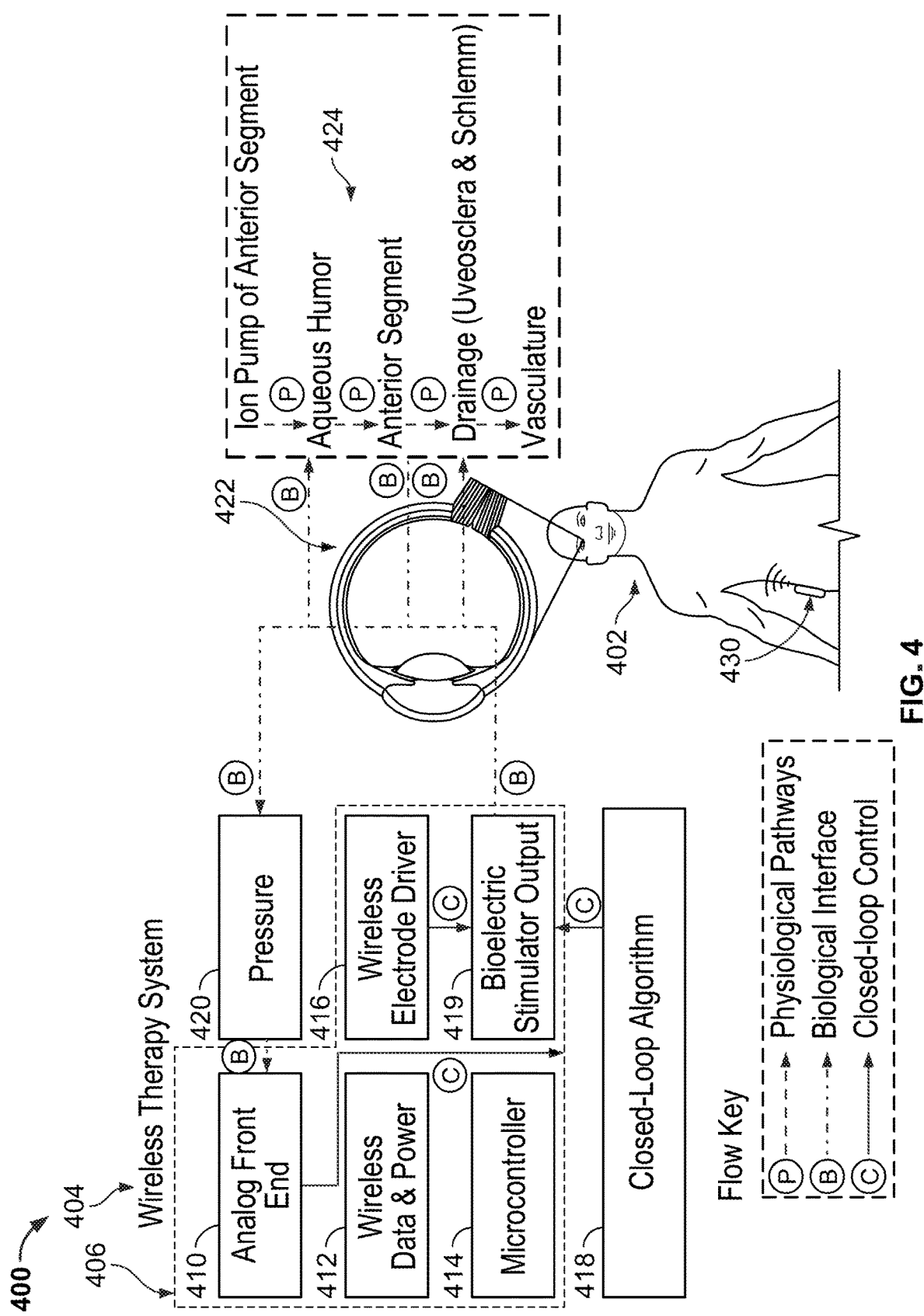
FIG. 4 shows a block diagram of a closed-loop wireless glaucoma therapy system, including various components and the resulting biological effects, according to an exemplary embodiment.

FIG. 4 shows a block diagram of an example of a closed-loop wireless glaucoma therapy system 400, including various components and the resulting biological effects. The wireless glaucoma therapy system 400 includes a controller system 404 (in dashed lines) with various components and circuitry to effectuate a closed-loop algorithm 418 for the monitoring and adjusting the glaucoma therapy based on feedback provided by a wireless pressure sensor 420 (described below) implanted within the eye 422 of the patient.

More specifically, the stimulator output 419, for example, will transmit a given time-varying electromagnetic field into the eye 422 (via WPT coil 130 and optionally stimulus coil 140) depending upon any number of input parameters and/or instructions being acted upon by the microcontroller 414 (e.g., input from the wireless IOP sensor 420 via the analog front end 410). By operating in a closed-loop manner, the wireless glaucoma therapy system 400 can dynamically influence the various physiological pathways 424 to achieve a desired decrease in aqueous humor inflow into and/or increase in aqueous humor outflow from the anterior segment of the eye 422.

In one embodiment, the wireless glaucoma therapy system 400 may be programmed and/or controlled by the patient and/or a physician via a mobile device 430 (e.g. iPhone by Apple, Inc., Galaxy by Samsung, Inc., iWatch by Apple, Inc., etc.) with software capable of wirelessly controlling the function of certain (or all) components of the wireless glaucoma therapy system 400. For example, it is contemplated that the components of the controller system 404 may be disposed on or within the various devices for positioning a WPT coil 130 in proximity to the eye 422 of the subject 402 (e.g. glasses, optical frames, sleep mask, pillow). In this case, the mobile device 430 could be used to wirelessly control the operation of the controller system 404, such as via Bluetooth connectivity between the mobile device 430 and the controller system 404.

The controller system 404 can include components to provide wireless data and power (412) that permits the control device 406 to wirelessly output data to a base station (separate from the mobile device 430) and to be wirelessly powered and/or charged. This output data can include a variety of different patient data, such as a log of conditions detected and therapies delivered, alerts as to currently detected conditions (e.g., elevated IOP), and/or other data. The controller system 404 can transmit this data wirelessly. The controller system 404 can be powered wirelessly (e.g., via RF signals) and can additionally include a local power source (e.g., battery) that can be charge via the wireless signals and that can power the controller system 404 when the wireless signal is unavailable.

The controller system 404 includes an analog front end 410 that receives wireless signals transmitted by the wireless IOP sensor 420. The analog front end 410 provides the received signals to the signal processing subsystem of the microcontroller 414. Signal processing can be performed onboard or offboard, and can involve using a closed-loop algorithm 418, which can be used to identify particular physiological conditions within the patient 402 and can determine, based on the particular detected conditions, whether to modify or alter the bioelectric stimulation at one or more WPT coils located in proximity to the eye 422 and optionally one or more stimulus coils disposed on or within the eye 422.

The closed-loop algorithm 418 can use any of a variety of appropriate techniques to learn the particular physiology of the patient 402 and the patient's particular response to therapy, and can use that information to determine when, how, and under what conditions to provide therapy for the patient 402. For example, the closed-loop algorithm 418 can be initially calibrated for the patient by a physician or other trained technician in a clinical setting, which can involve providing various stimulations and recording the physiological response of the patient 402. After being initially calibrated, the closed-loop algorithm 418 can continue to learn and adapt over time by analyzing data generated by the wireless IOP sensor 420, therapy provided to the patient 402, and the patient's response to the therapy. The closed-loop algorithm 418 can repeatedly monitor patient data and apply stimulation to the ion pump and/or eye muscles (e.g., eye muscles affecting eye drainage) when appropriate until the patient's elevated IOP condition has been reduced and/or dropped below a threshold level. The closed-loop algorithm 418 can be automatically implemented without explicit patient direction.

Figure 5:
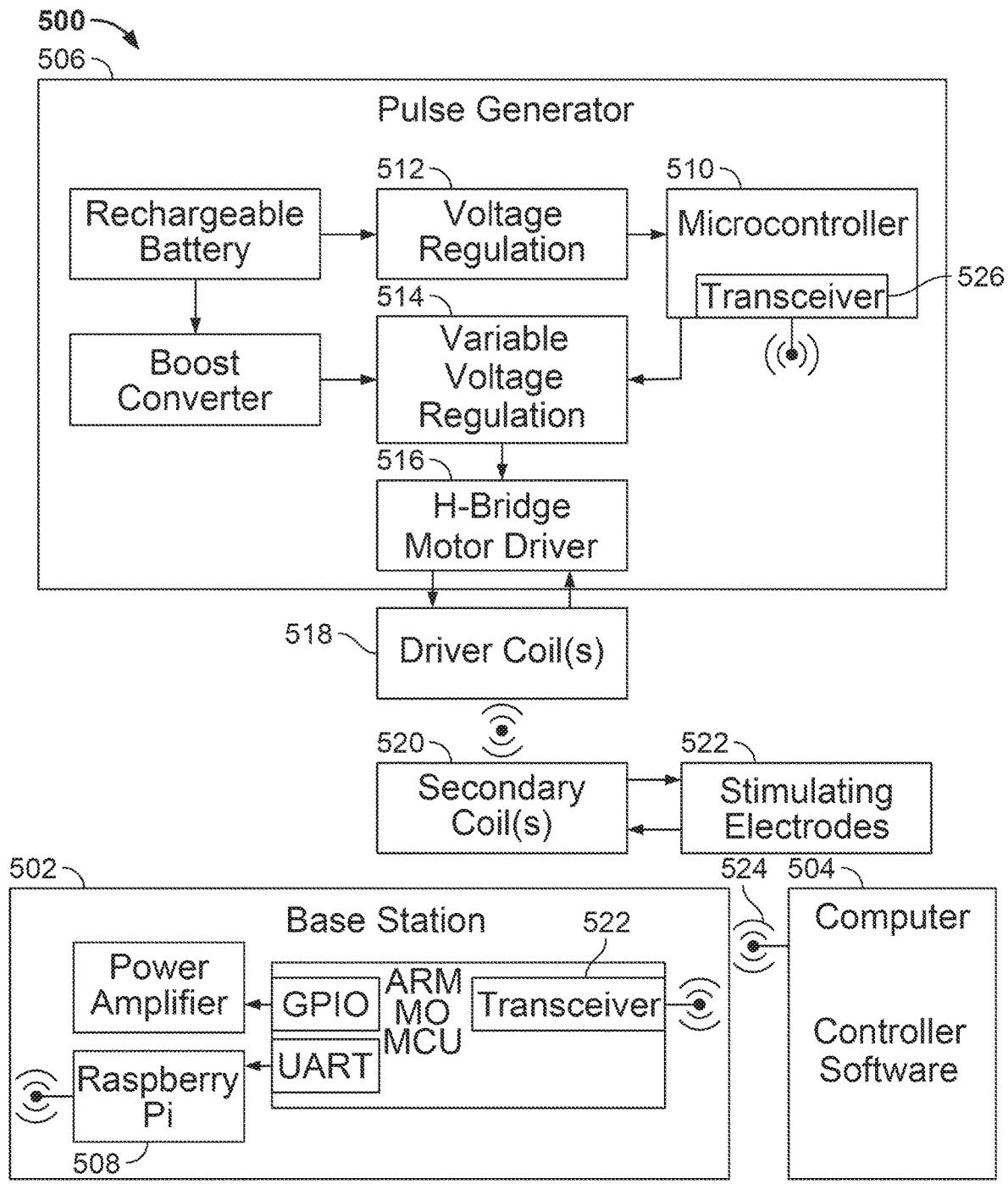
FIG. 5 shows a wireless power transfer (WPT) system of the wireless glaucoma therapy system of FIG. 1, including base station and signal generator, according to an exemplary embodiment.

FIG. 5 shows an example of an open-loop wireless glaucoma therapy system 500, including various components. The wireless glaucoma therapy system 500 includes a base station 502, a computer 504, and a pulse generator 506. The base station 502 and computer 504 cooperate to wirelessly transmit control signals to the pulse generator 506 to effectuate control programming set forth in software being executed by the computer 504. The base station 502 may be wirelessly connected to the pulse generator 506 via any suitable wireless communication technology or system (e.g. Raspberry Pi 508) capable of wirelessly communicating with a microcontroller 510 of the pulse generator 506. The base station 502 may also be wirelessly connected to the computer 504, using transceiver 522 and its associated antenna along with another transceiver and associated antenna 524 provided with the computer 504. It will be appreciated that, although shown with wireless communication between the base station 502 and the computer 504, as well as between the base station 502 and the pulse generator 506, any or all of these wireless communications pathways may be replaced via physical communications links (e.g. computer cable).

The pulse generator 506 receives the wireless control communications from the base station 502 via a transceiver 526 in communication with (or forming part of) the microcontroller 510. The microcontroller 510 cooperates with circuitry (e.g. voltage regulation 512, variable voltage regulation 514) to drive an H-bridge driver 516 coupled to one or more drive (WPT) coils 518 to transmit a time-varying electromagnetic field. This electromagnetic field may be administered to the eye via drive (WPT) coil(s) 518 positioned in proximity to the eye and optionally via one or more secondary coils 520 located on or within the eye. Through the principles of wireless electromagnetic energy (e.g. inductive, far-field RF, optical, etc.) coupling, the secondary coils 520 may be adapted to receive the time-varying electromagnetic field from the drive (WPT) coils 518 and transmit that energy into ocular structures of the eye via one or more stimulating electrodes 522 disposed on or within the eye, as discussed in detail below. Whether WPT-only (that is, drive/WPT coils 518 alone) or WPT in combination with secondary (stimulus) coils 520, the wireless glaucoma therapy system 500 is capable of administering a therapeutically effective amount of energy to achieve the desired reduction in aqueous humor inflow into and outflow from, respectively, the anterior segment of the eye.

Figure 6:
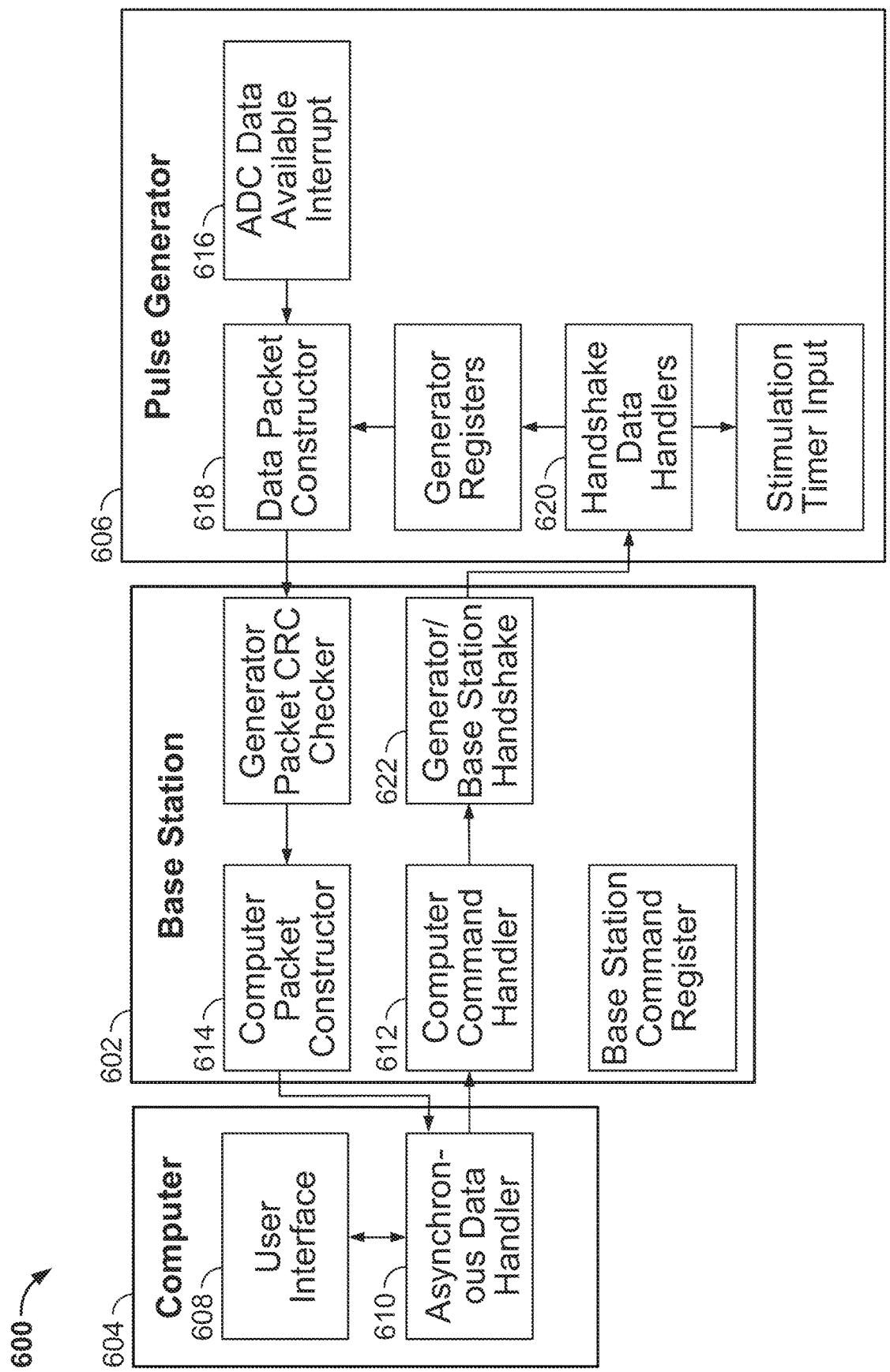
FIG. 6 shows a diagram of the communication pathway of the wireless glaucoma therapy system of FIG. 1, according to an exemplary embodiment.

FIG. 6 shows a diagram of depicting an example of the communication pathway between the components of a wireless glaucoma therapy system 600 of the type shown in FIG. 5, with base station 602, computer 604, and pulse generator 606. The communication within wireless glaucoma therapy system 600 starts on the left, with a user interfacing with the computer 604 such as inputting instructions or the like via User Interface 608 (e.g. keyboard, GUI, etc . . . ). The computer 604 is communicatively linked with the base station 602 via an asynchronous data handler 610 that sends output signals to a computer command handler 612 and receives input signals from a computer packet constructor 614.

Bidirectional communication during use of the system can greatly increase the flexibility and possible application use of an implantable device such as the wireless IOP sensor described herein, which would be coupled to the analog-to-digital converter (ADC) Data Available Interrupt module 616. The ability to transmit data potentially removes the burden of on-board data storage from the implantable device, but it also allows the implantable device to communicate its current status and settings in real time, allowing for increased confidence in implant performance over time. Furthermore, the ability to receive data allows the implantable device to be configured, calibrated, and instructed before, during, and after implantation; increasing its adaptability to varying circumstances. An implantable device that can both receive and transmit data (such as the wireless IOP sensor) has the added benefit of allowing an external user or system to reactively send instructions to the implantable device based off of recorded data obtained by the implantable device; effectively creating a closed-loop system.

Bidirectional communication can be performed, as illustrated in FIG. 6, by enforcing a coordinated handshake protocol with a custom designed external base station 602 which facilitates all communications with any outside user.

After the pulse generator 606 acquires a specific number of samples, for example 40 data samples, from its analog-to-digital converter (ADC) Data Available Interrupt 616, a microcontroller with the pulse generator 606 initiates a data-packet transmission to the base station 602 using an on-board radio. Data packets can be constructed, for instance using conventional packetization techniques, to include recoded data, and subsequently communicated via transmission signal from a data packet constructor 618.

After a successively transmitting multiple packets, for instance the 100th data packet, the pulse generator 606 initiates a hand-shake with the base station 602. The handshake can be performed between respective handshake units (620, 622). After transmitting a specified data packet, or a data packet otherwise deemed as the end of communication (e.g., 100th data packet), the pulse generator 606 sets its radio to receive mode, and listens for a data packet from the base station 602 for a time, typically not exceeding 10 milliseconds. This gives the base station 602 an opportunity to send a single data packet to the pulse generator 606. The data packet can contain a 45-byte long payload, which is used to set firmware registers in the microcontroller of the pulse generator 606 that stores data acquisition, stimulation, and communication settings.

In some cases, the handshake driven communication scheme allows the pulse generator 606 to transmit acquired data rapidly, while maintaining the ability to receive data from an outside source with minimal radio activation time. For example, given a total data acquisition sample frequency of 5 kHz, the radio of the pulse generator 606 will transmit 125 data packets per second and initiate a handshake once every 800 milliseconds. Given the radio on-time described above, bidirectional communication is achieved with the radio being deactivated at least 86.7% of the time.

Another challenge in a wireless communication scheme is increasing data robustness. In order to properly analyze any data recorded by the pulse generator 606, the ability to identify when data has been corrupted or lost may be desired. Data can be corrupted or lost during wireless transmission in various conditions, including: if it is obstructed by a blockage that can absorb RF energy; if a nearby device communicating on the same frequency creates interference; and if the distance between the pulse generator 606 and the base station 602 exceeds the transmission range of the pulse generator 606. Furthermore, data can be lost in the scenario if the pulse generator 606 suddenly loses power during data acquisition or transmission.

Figure 7:
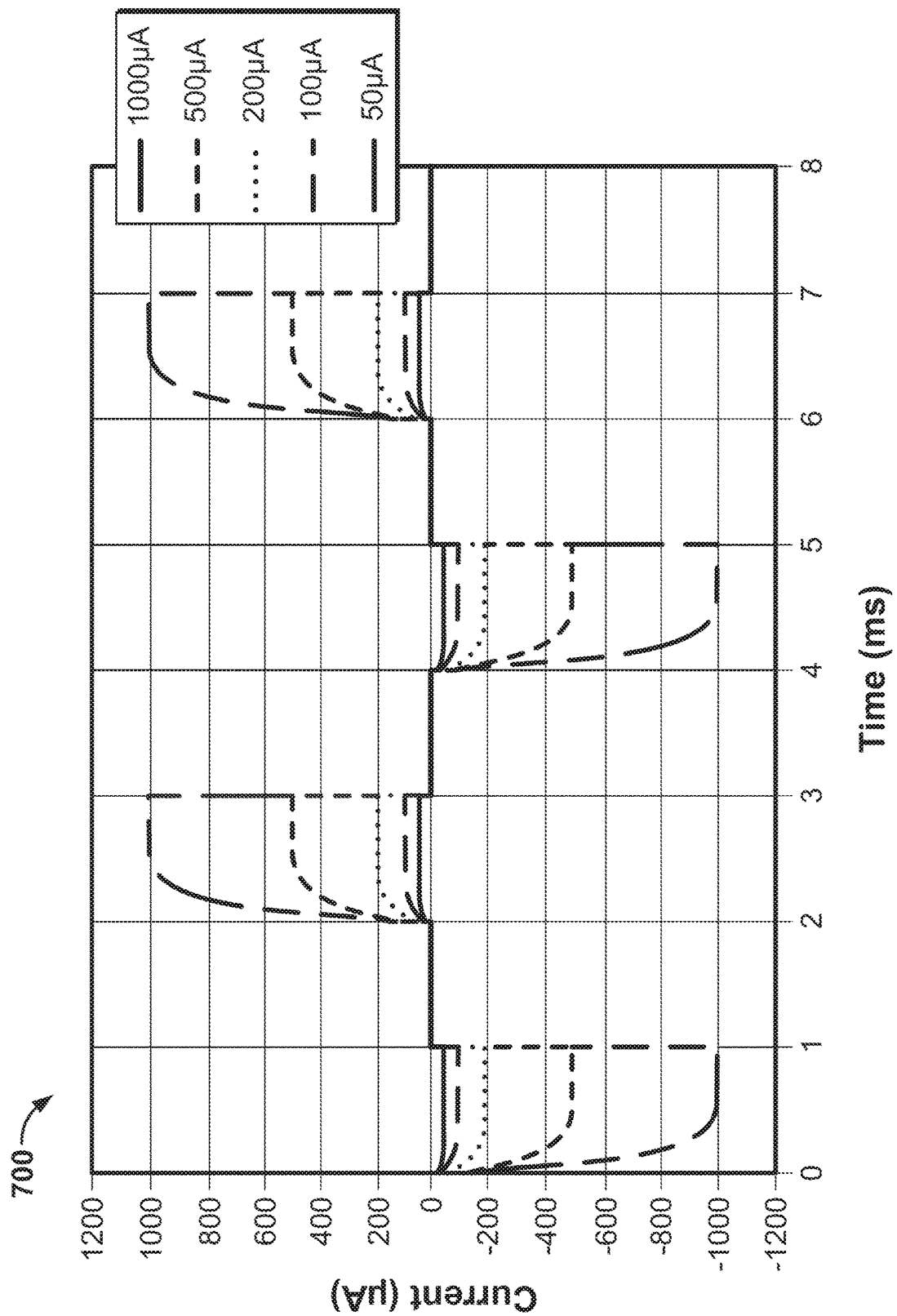
FIG. 7 shows a graph displaying current-controlled, biphasic output measured from the stimulator outputs aspect of the wireless power transfer system of FIG. 1, according to an exemplary embodiment.

FIG. 7 shows an example graph 700 displaying current-controlled, biphasic output measured from the stimulator outputs aspect of the wireless power transfer system. In this example, the stimulator output is measured on a benchtop using a 10 kΩ load across the stimulator outputs. The graph 700 displays the output signal as a relationship between time (ms), along the X-axis, versus current (µA) along the Y-axis. Pulse width, current amplitude, and duty cycle can be selectable parameters in real-time through reverse telemetry from the base station to the WPT coil or other suitable wirelessly powered device. A pulse width of 1 ms and a 50% duty cycle are used here to illustrate the current output for a range of amplitude settings.

FIGS. 8-16 illustrate several manners of positioning a WPT coil (e.g., coil 130 shown in FIG. 1) near the eye to enable the administration of wireless glaucoma therapy according to the principles set forth herein. These include, but are not necessarily limited to, glasses with WPT coil(s) for administering wireless glaucoma during normal activities of daily living (e.g. FIGS. 8 and 10), WPT coil(s) on an optical frame used by ophthalmologists and/or optometrists in a clinical setting (e.g. FIG. 9), and devices to enable the administration of wireless glaucoma therapy while the subject is sleeping, such as WPT 130 as part of a sleep mask (FIG. 15), pillow (FIG. 16), etc. In each case, the WPT coil delivers the time-varying electromagnetic field to the eye in a therapeutically effective amount to reduce the IOP within the eye by decreasing the inflow and/or increasing the outflow of aqueous humor into and out of, respectively, the anterior segment of the eye.

Whether disclosed below for "WPT-Only" usage or with stimulus coils as well, it will be appreciated that the embodiments shown and described herein may be provided in combination with a host of additional features. For example, a wireless IOP sensor may be provided to monitor the IOP and regulate or modify the delivery of therapy in a closed-loop manner. A Fresnel lens may also be employed on the glass lenses to focus incoming light rays onto the retina of the eye for the purpose of vision correction. The Fresnel lens may be constructed with a series of metallic traces (in order to achieve vision correction) which makes the Fresnel lens capable of receiving the time-varying electromagnetic fields. The Fresnel lens may be employed with the WPT system (including WPT coil) in order to deliver glaucoma therapy in addition to vision correction.

Figure 8A:
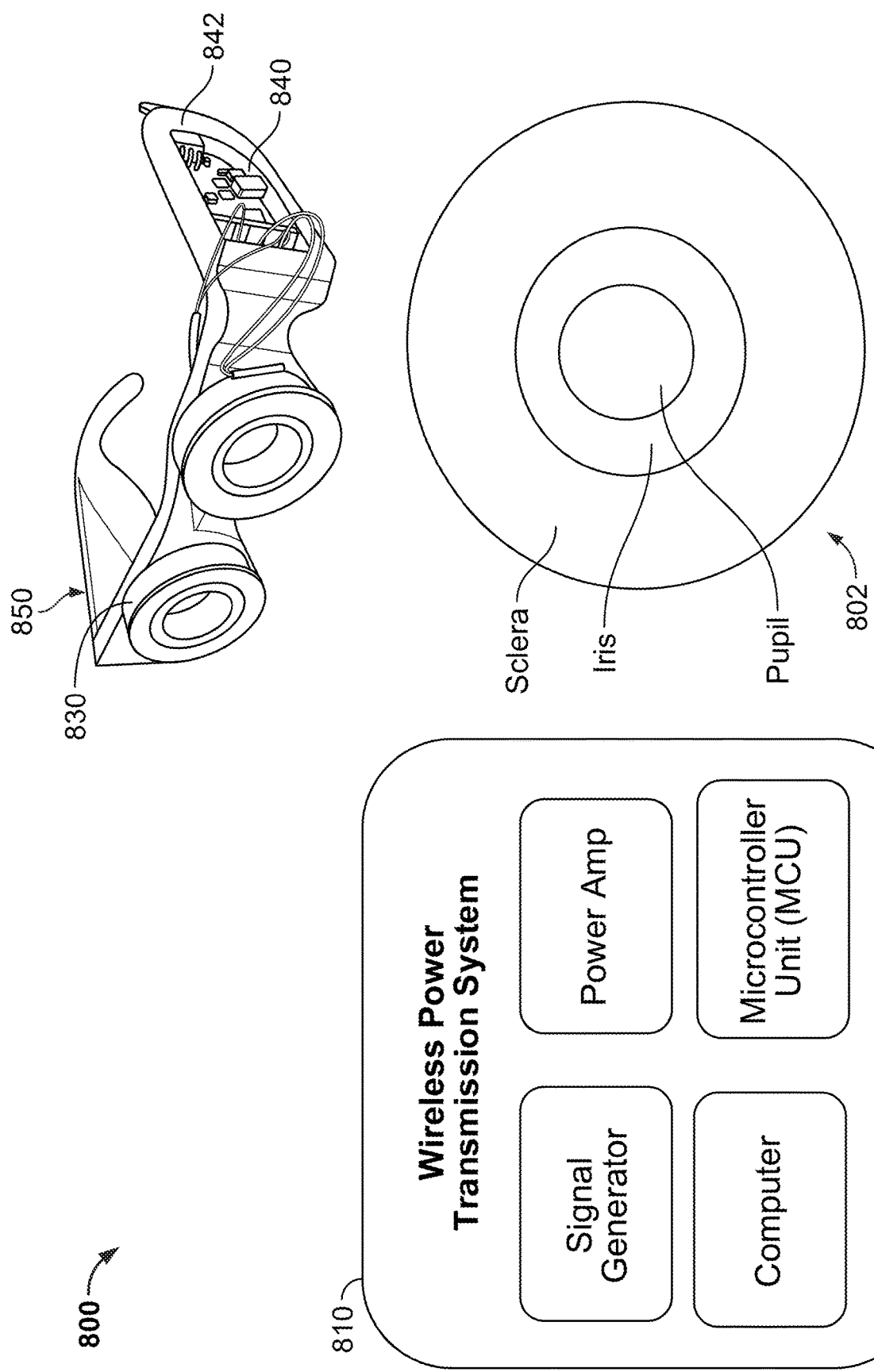
FIGS. 8A-8E show a wireless glaucoma therapy system involving the use of a wireless power transfer (WPT) coil associated with glasses for implementing the disclosed techniques, according to an exemplary embodiment.

FIG. 8A shows an example wireless glaucoma therapy system 800 includes a wireless power transfer (WPT) system 810 for generating time-varying electromagnetic fields and transmitting them to wireless power transfer (WPT) coils 830. Each WPT coil 830 is disposed on a frame of the glasses 850 and configured to deliver the time-varying electromagnetic fields to the eye 802 of a mammalian subject. The coils 830 are disposed on the frame of the glasses 850 at a fixed distance above the eye 802 and are aligned coaxially about an axis passing through the approximate center of the viewing aperture of the glasses. This serves to increase efficiency and consistency of the electromagnetic field exposure to the ocular structures within the eye 802 of the mammalian subject. The WPT coils 830 include viewing apertures to coincide with the viewing apertures of the glasses, such that a wearer of the glasses can still see while receiving wireless glaucoma therapy according to the disclosed techniques.

In this embodiment, the glasses 850 are equipped with a pulse generator 840 (e.g., of the type shown and described with reference to FIG. 5) disposed within a housing 842 formed on one leg of the glasses 850. The WPT system 810 may include circuity and components similar to the base station 506 of the type shown and described with reference to FIG. 5. Instead, such base station circuitry and components could form part of an "app" for a mobile device (e.g. iPhone by Apple, Inc., Galaxy by Samsung, etc . . . ), including the ability to communicate with the pulse generator 840 via any suitable Bluetooth communication technology (e.g. Raspberry Pi).

Figure 8B:
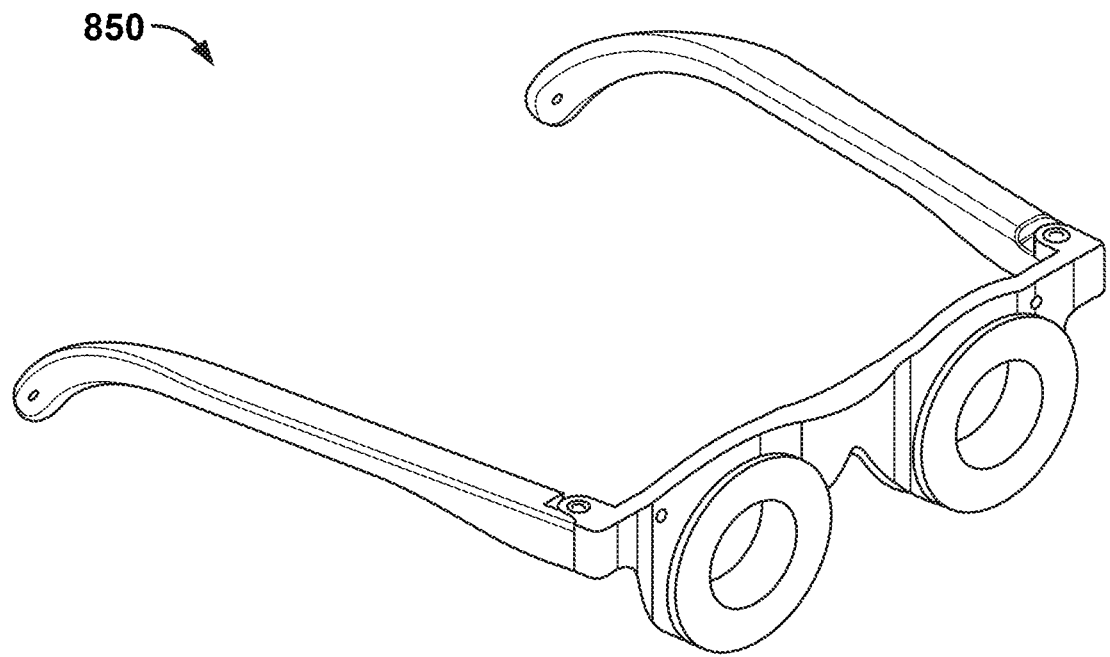
Figure 8C:
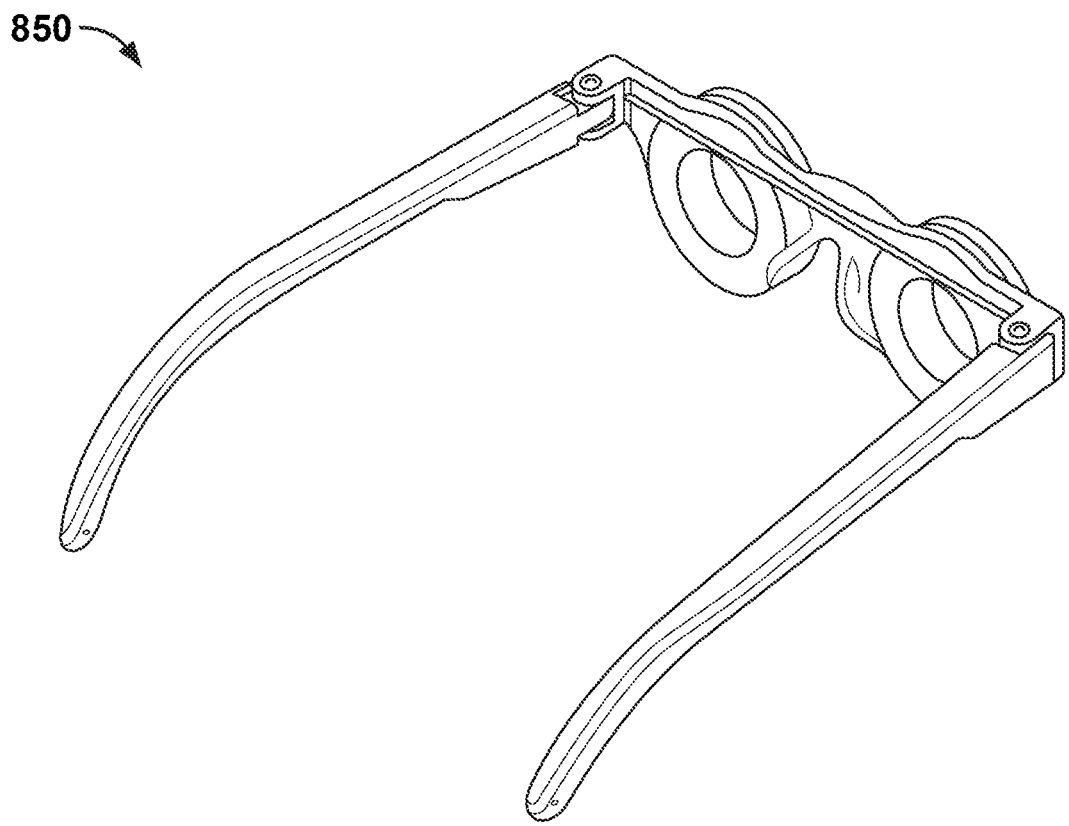
Figure 8D:
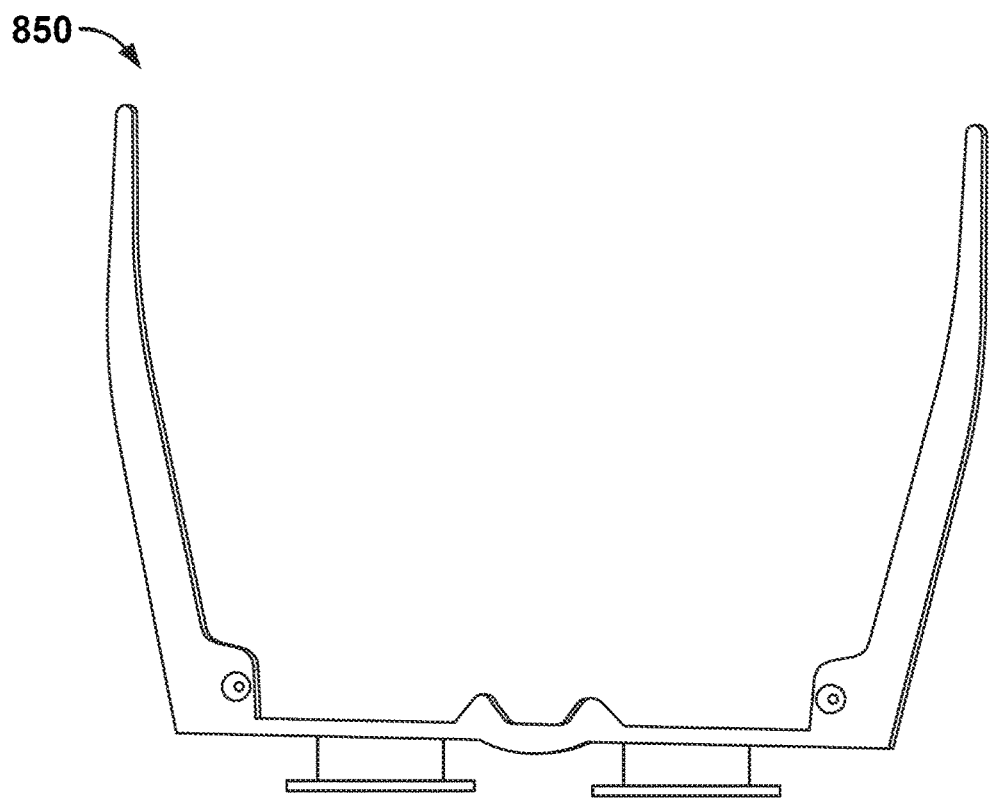
Figure 8E:
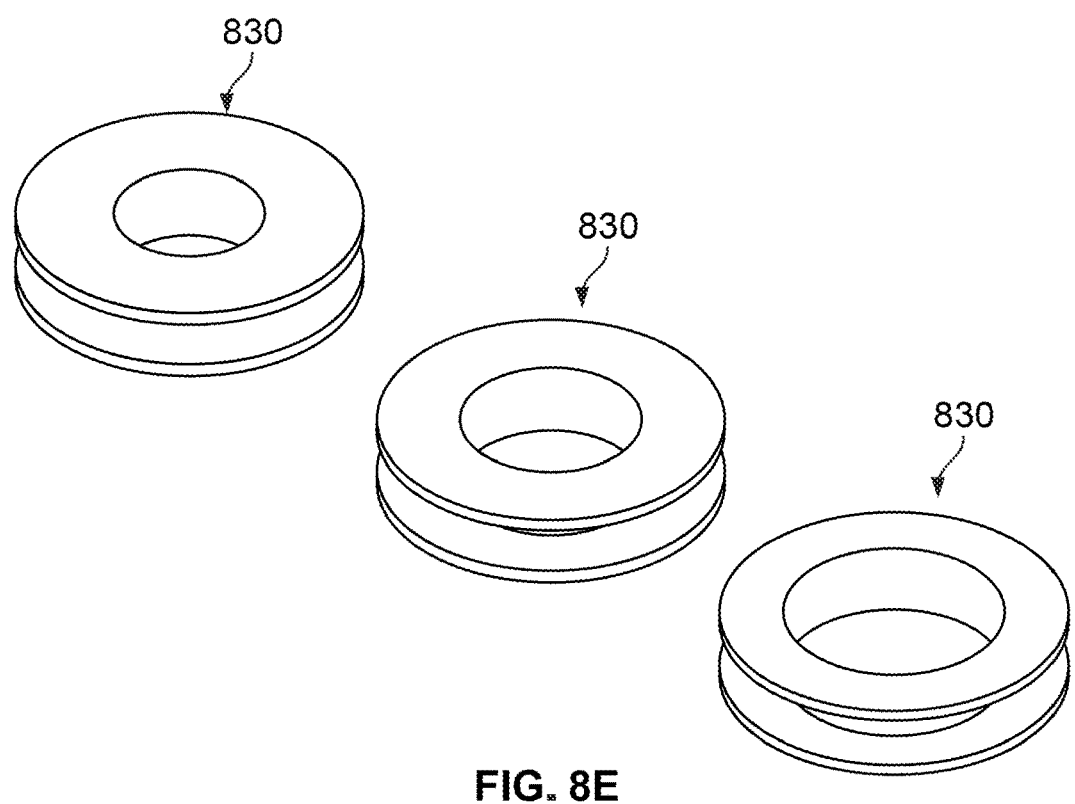

FIGS. 8B-8D show an alternate embodiment with the main difference that the glasses 850 do not include the on-board pulse generator 840 and the WPT coils 830 (FIGS. 8D and 8E) may be removably attached to the glasses 850. This allows the user and/or healthcare professional to increase or decrease the range of electromagnetic fields by simply changing the existing WPT coil 830 to one with a more suitable size or number of turns (larger and higher for increased magnetic field, and smaller and lower for lower magnetic field). It also decreases the weight of the glasses 850 (by removing the pulse generator, batteries, etc.).

FIGS. 9A-9E show an alternate embodiment for positioning WPT coils in proximity to the eye of a mammalian subject, this time involving the use of an optical frame 930 rather than the glasses 850 of FIG. 8. Other than this change, in most respects the wireless glaucoma therapy system 900 is similar to wireless glaucoma therapy system 800 of FIG. 8 such that a full description need not be repeated. The depicted wireless glaucoma therapy system 900 of FIG. 9A includes a wireless power transfer (WPT) system 910 (depicted in a block diagram), for generating time-varying electromagnetic fields and transmitting them to one or more WPT coils 920. The one or more WPT coils 920 are disposed on the optical frame 930 and configured to deliver the time-varying electromagnetic fields to the eye 902 at a desired distance away from the eye 902. In one embodiment, the WPT system 910 and WPT coils 920 are capable of transmitting time-varying electromagnetic fields to the eye 902 at a sufficient level and manner to result in a decrease in the IOP. This decrease in IOP is based on a fluid outflow increase and possibly also a fluid inflow decrease.

A stimulus driver connector 932 can be coupled to WPT coils 920 mounted on or otherwise carried by the optical frame 930 such that the WPT coil 920 may be hard-wire connected to the WPT system 910. A direct connection to the stimulus driver 934 may provide a higher level of energy transmission into the eye 902, which can result in IOP reduction in a shorter time period or to a greater extent than that accomplished by the WPT system 910 and WPT coil 920 alone. In some embodiments, a stimulus coil (not shown) may be disposed and configured in one or more components of the optical frame 930 such that the stimulus coil is positioned near the eye 902.

Figure 9A:
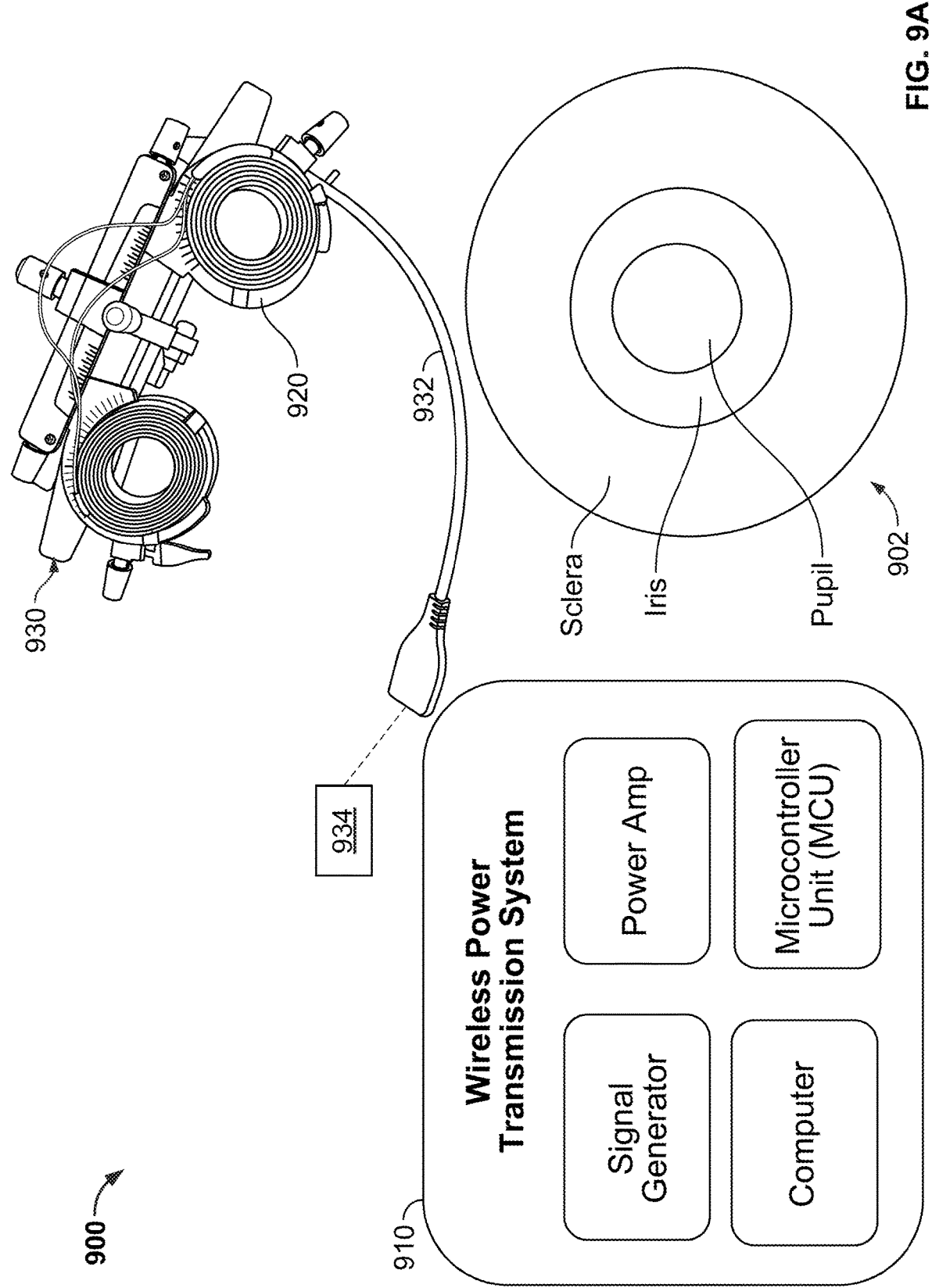
FIGS. 9A-9E show a wireless glaucoma therapy system involving the use of a wireless power transfer (WPT) coil associated with optical frames for implementing the disclosed technique, according to an exemplary embodiments.
Figure 9B:
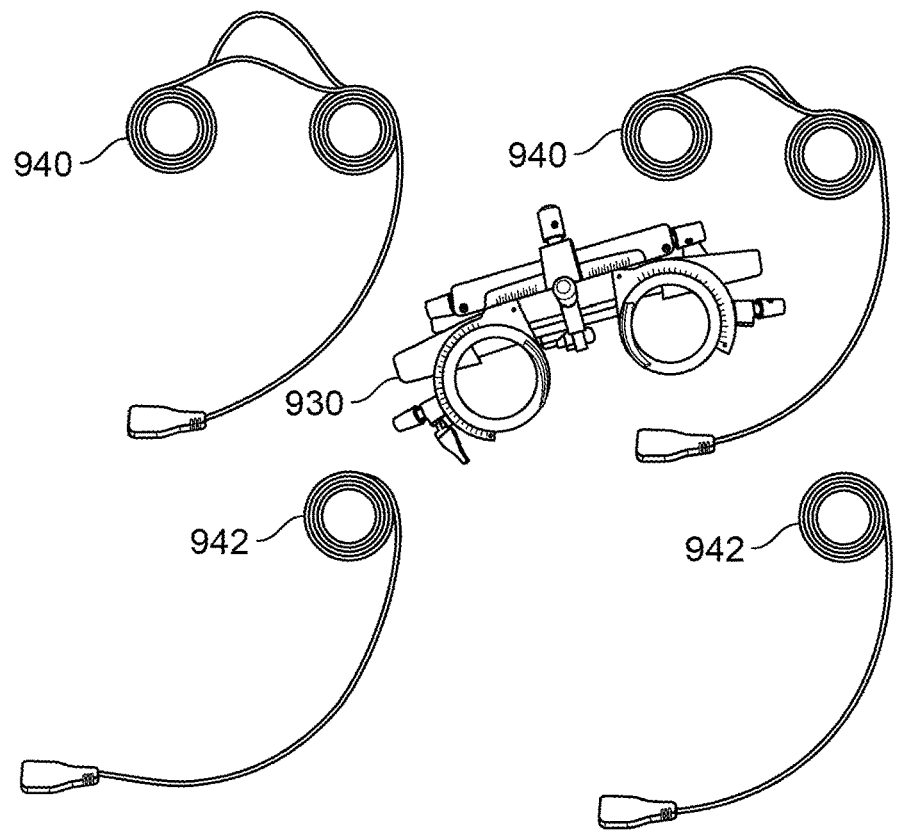

FIG. 9B shows a magnified image of the wireless glaucoma therapy system 900, showing the optical frames 930 carrying a single WPT coil 920. This may be useful when providing wireless glaucoma therapy to a patient in a clinic setting, such as the office of an ophthalmologist and/or optometrist, to administer the wireless glaucoma therapy to a single eye rather than both (e.g. to isolate and assess or deliver therapy in a targeted manner).

In some embodiments, the wireless glaucoma therapy system 910 does not obstruct vision and is wearable, comfortable, and discrete. The operation of the system 910 occurs based on a phenomena of induced electrical currents on conductors in the presence of time-varying magnetic fields. The coils 920 fitted to the frames 930 are constructed of wound, enamel-covered copper wire. The coils 920 may be constructed to have any number of suitable characteristics, including (by way of example only) a weight in the range of 15-25 grams, a resistance in the range of 0.5 Q to 1.5 Q, and an inductance in the range of 150 uH to 450 uH. The coils 1120 are connected to an external circuit board equipped with one or more battery, a microcontroller, and circuitry for the generation of pulsed magnetic fields to excite specifically-tailored electrical currents on the passive circuitry of the frames.

The optical frame can comprise commercially available optical frames, for example, the "Optometry Optician Fully Adjustable Frame" offered by Vktech, Inc. The frames can be equipped with fitted coils 920 (as shown in the photo image shown in FIG. 9A) to provide the wireless power.

The optical frame 930 can include a range of desired frame specification and dimensions. One or more of the following non-limiting frame specifications and dimensions can be applied in certain embodiments: (1) range of PD adjustments (e.g., PD of both eyes ranging from about 48 to 80 mm, left or right PD ranging from about 24 to about 40 mm minimum (2) a graduated value of about 1 mm; (3) a dividing disc axial graduation; (4) a left dividing disc of 120°~0°~135°; (5) right dividing disc of 45°~180°~60°; (6) axial graduation increases along the lens frame axis counter-clockwise, and the graduated distance being about 5°; (7) an inner diameter of lens frame of about 32.5 mm; (8) the number of lens that can be inserted into left or right lens frame simultaneously can be 4 pieces; (9) the degree of lens rotating around optical axis in the lens frame can be 360°; (10) non-parallelism between lens' optical axis and lens frame's geometric axis can be less than or equal to 2.5°; (11) non-concentricity between lens' optical center and lens frame geometric center can be less than or equal to 0.5 mm; (12) displacement of lens in relation to position of lens frame geometric center can be less than or equal to 0.3 mm; (13) a range of nose rest adjustment can include a length of about 0 to about 14 mm and an angle of about 0° to about 30°; (14) a range of left or right lens frame leg's length adjustment can range from about 98 mm to about 135 mm; (15) a maximum interval between left and right lens frame legs can be about 200 mm; (16) the material can be a lightweight metal or plastic; (16) any desirable color or mix of colors can be used (e.g., black and silver); and (17) the size can be 15.50*6.00*3.50 cm.

Figure 9C:
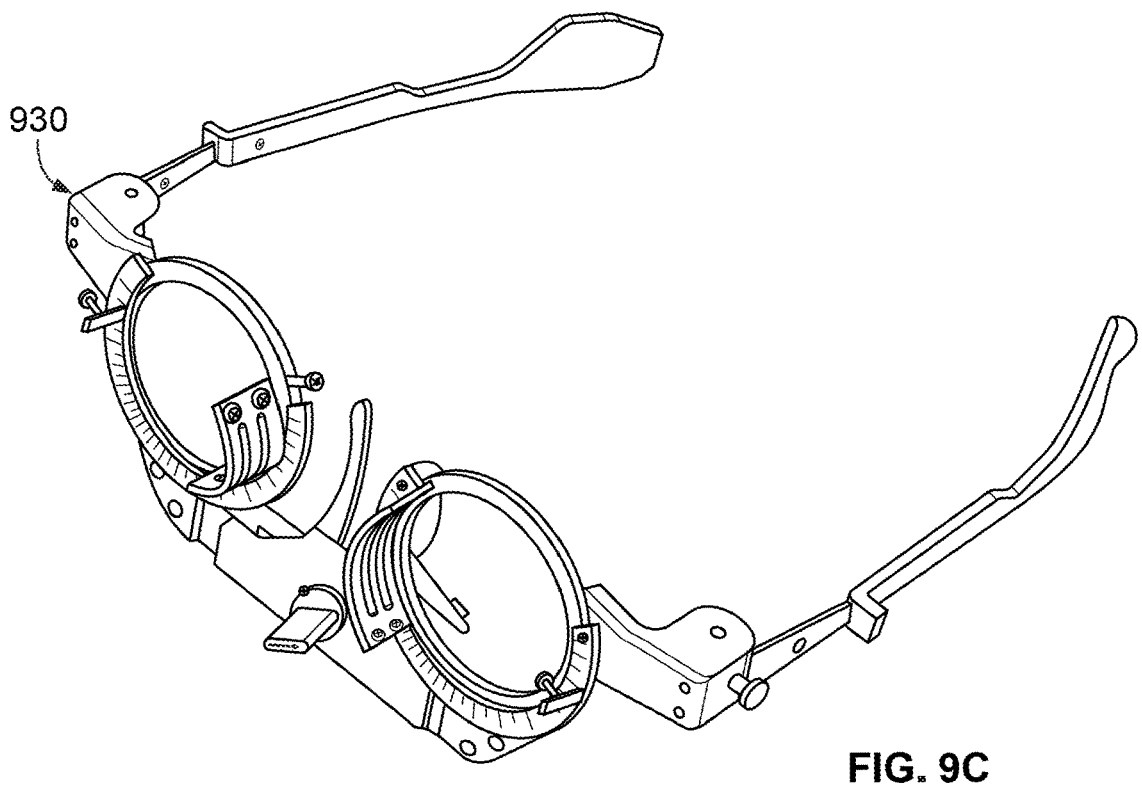
Figure 9D:
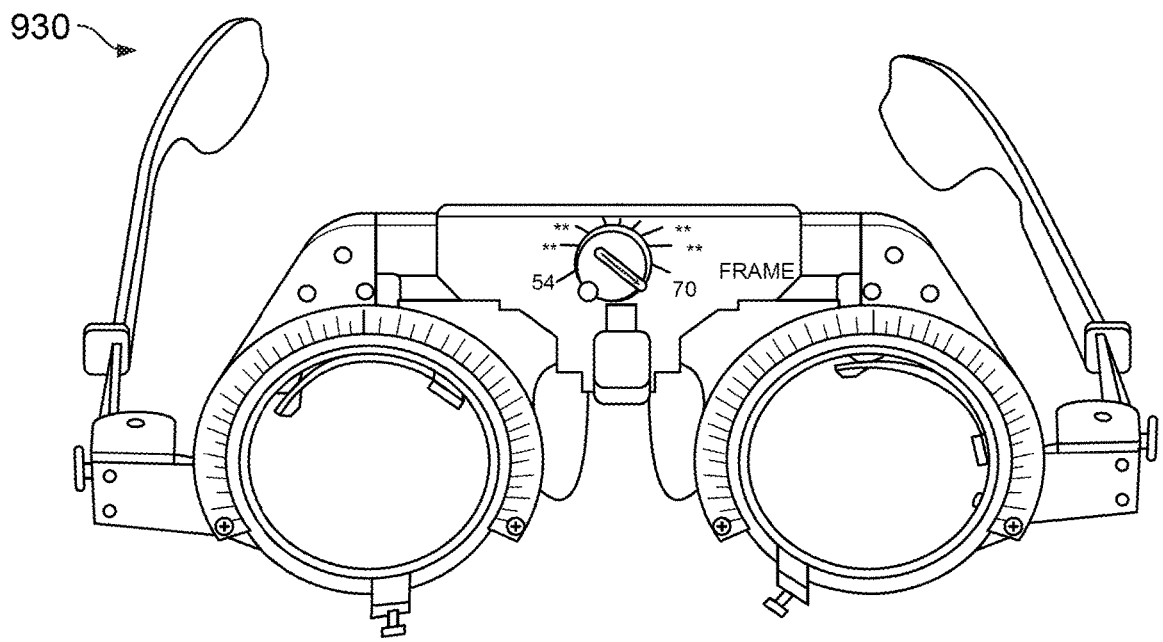
Figure 9E:
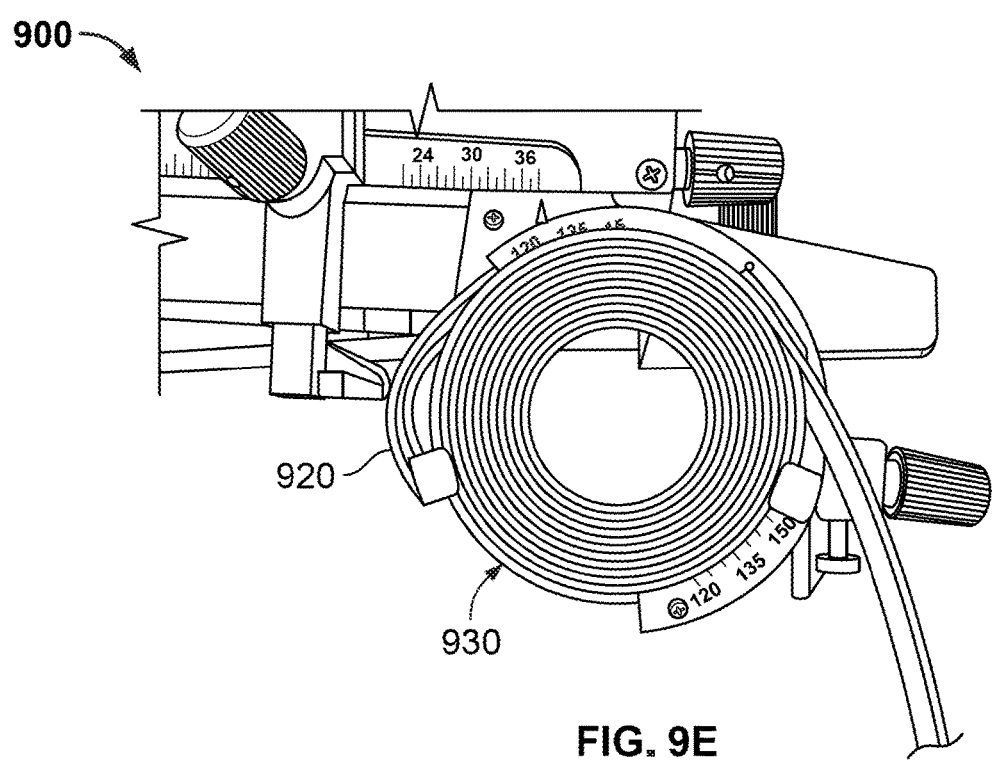

FIGS. 9C and 9D show different views of an example optical frame 930 (without the coils 920) that can be used with the wireless glaucoma therapy system 900. FIG. 9E shows an example optical frame 930 along aside with two dual-coil assemblies 940 and two single-coil assemblies 942. In some embodiments, the optical frame 930 can use one dual coil assembly 940, or one or two single-coil assemblies 942.

Figure 10:
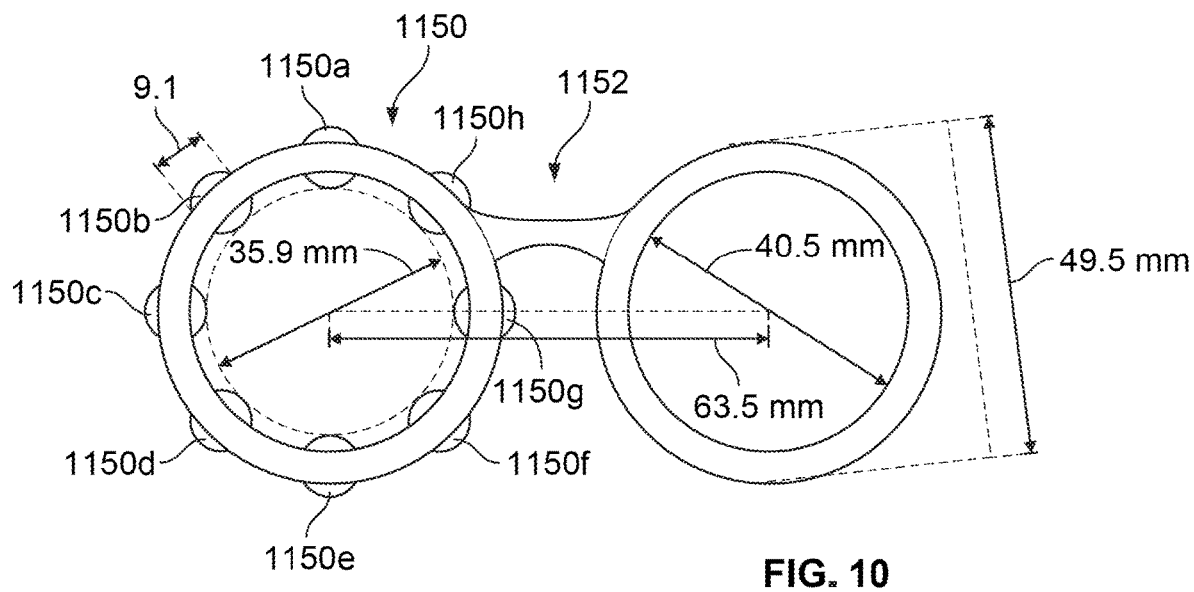
FIG. 10 shows a front view of a WPT coil assembly configured for use with glasses, where the coil assembly includes multiple pairs of electrical coils e.g., 4 pairs), according to an exemplary embodiment.

FIG. 10 shows a front view of a multi-coil WPT assembly 1150 configured (by way of example only) for use with glasses 1152, wherein the multi-coil WPT assembly 1150 includes multiple pairs of electrical coils (by way of example only, 4 pairs) and forms part of a wireless glaucoma therapy system of the type(s) described above. Although shown with a single multi-coil WPT assembly 1150 on the glasses 1152, it will be appreciated that the glasses 1152 in practice may include a second multi-coil WPT assembly 1150 of the same or similar construction. In this embodiment, the multi-coil WPT assembly 1150 does not obstruct vision and is wearable, comfortable, and discrete given that is configured to be coupled to or otherwise form part of a traditional set of glasses 1152. The multi-coil WPT assembly 1150 includes a plurality of coils, by way of example only, eight coils denoted by reference numerals 1150a-1150h (the construction of which will be described in detail below). Although shown with the coils 1150a-1150h exposed or visible relative to the glasses 1152, it will be appreciated that the coils 1150a-1150h may be housed within or otherwise covered by a variety of structures or materials in order to obfuscate or otherwise de-emphasize the visual appearance of the coils 1150a-1150h.

Figure 11:
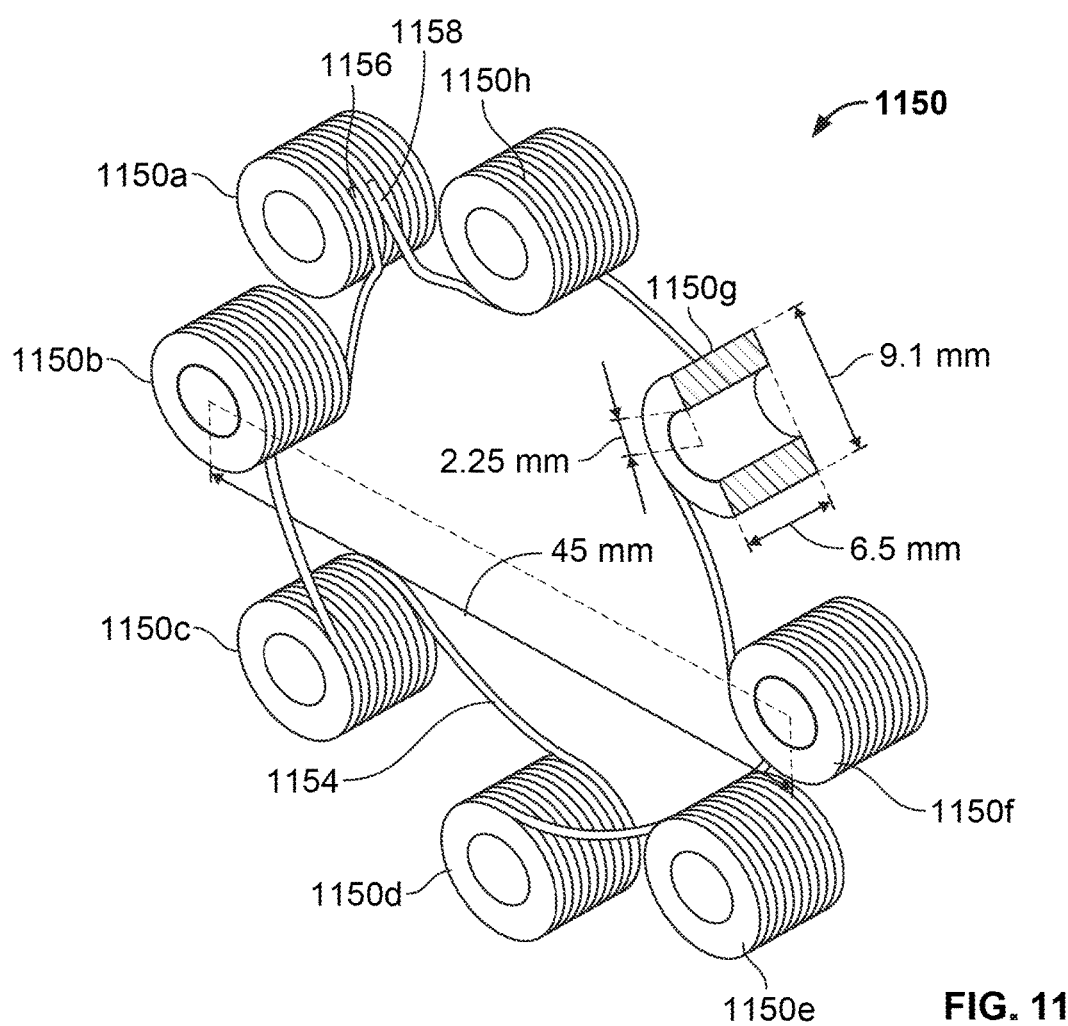
FIG. 11 shows a perspective view of the multiple pairs of electrical coils forming part of the WPT coil assembly as shown in FIG. 10, according to an exemplary embodiment.

FIG. 11 illustrates the multi-coil WPT assembly 1150 separate and apart from the glasses 1152 shown in FIG. 10. In this embodiment, the multi-coil WPT assembly 1150 is constructed of a single enamel-covered copper wire 1154 wound to create each of the coils 1150a-1150h with alternating winding directions between adjacent coils. More specifically, the windings that comprise coils 1150a, 1150c, 1150e, 1150g are constructed in a clockwise manner, while the windings that comprise coils 1150b, 1150d, 1150f, 1150h are constructed in a counter-clockwise manner. The coils 1150a-1150h may be constructed to have any number of suitable characteristics, including (by way of example only)

a collective weight in the range of 15-30 grams, a collective resistance in the range of 0.5 to 12 ohms (in one example, 9.9 ohms), and an inductance in the range of 150 uH to 800 uH (in one example, 773 uH). The copper wire 1154 includes a first terminal end 1156 and second terminal end 1158 which, in use, are connected to a wireless power transfer system of the types described above to deliver pulsed magnetic fields to the eye of a mammalian subject. As will be described in more detail below, by constructing the multi-coil WPT assembly 1150 such that the coils 1150a-1150h have alternating winding directions, the pulsed magnetic fields are driven into and out of the eye to induce rotating eddy currents at the point of impact on the eye surface. The resulting rotating eddy currents add to create radial current vectors through structures of interest within the eye of the mammalian subject, including (but not necessarily limited to) the ciliary body and/or Canal of Schlemm. By acting upon these structures of interest, the radial current vectors serve to reduce the IOP within the eye by decreasing the inflow and/or increasing the outflow of aqueous humor into and out of, respectively, the anterior segment of the eye.

Figure 12A:
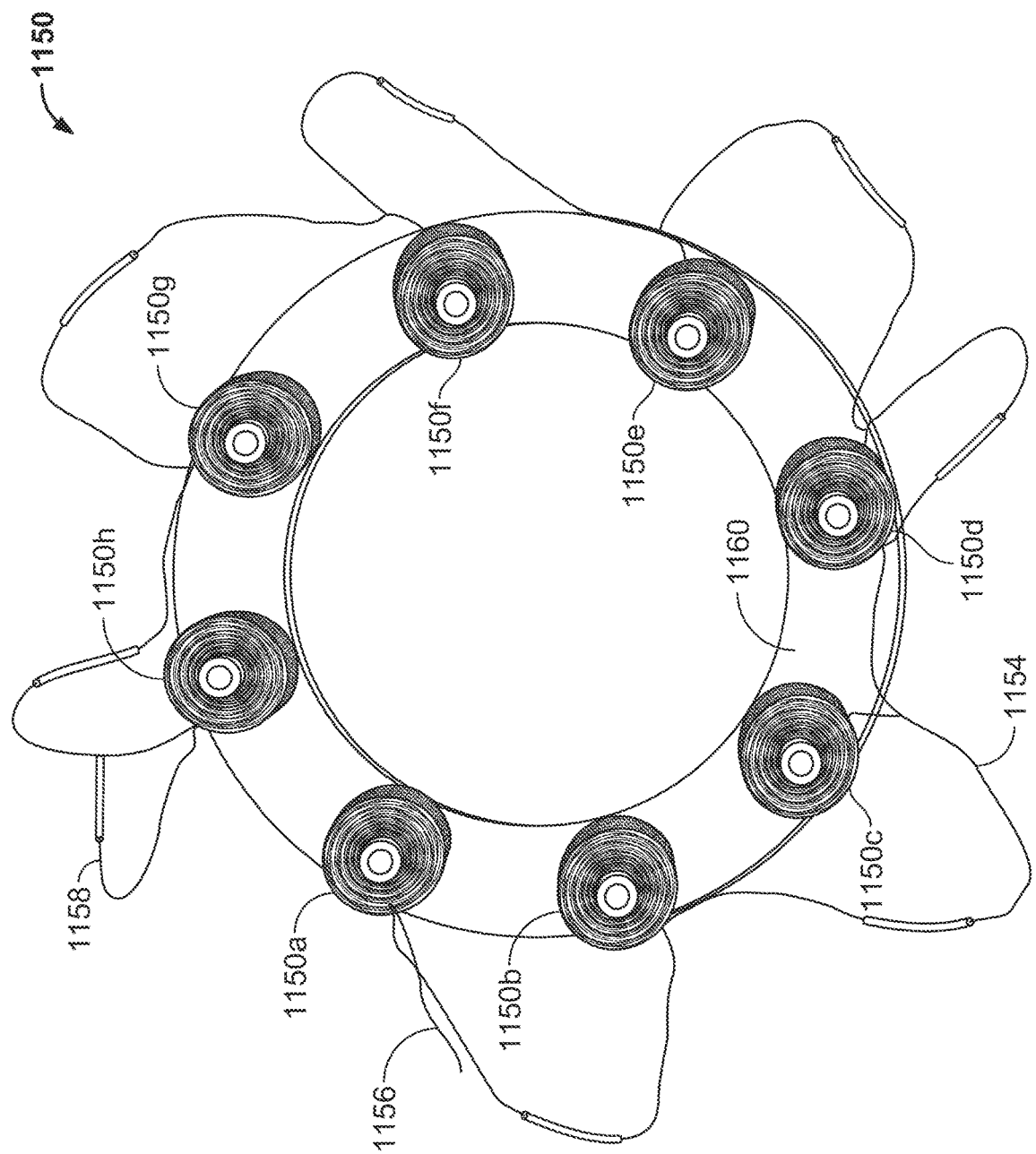
FIGS. 12A-12B show front views of the WPT coil assembly of FIG. 10 positioned on the hand of an investigator (FIG. 12A) to show scale, and positioned over the eye of a mammalian subject (FIG. 12B) to demonstrate the position of the WPT coil assembly during use, according to an exemplary embodiment.
Figure 12B:
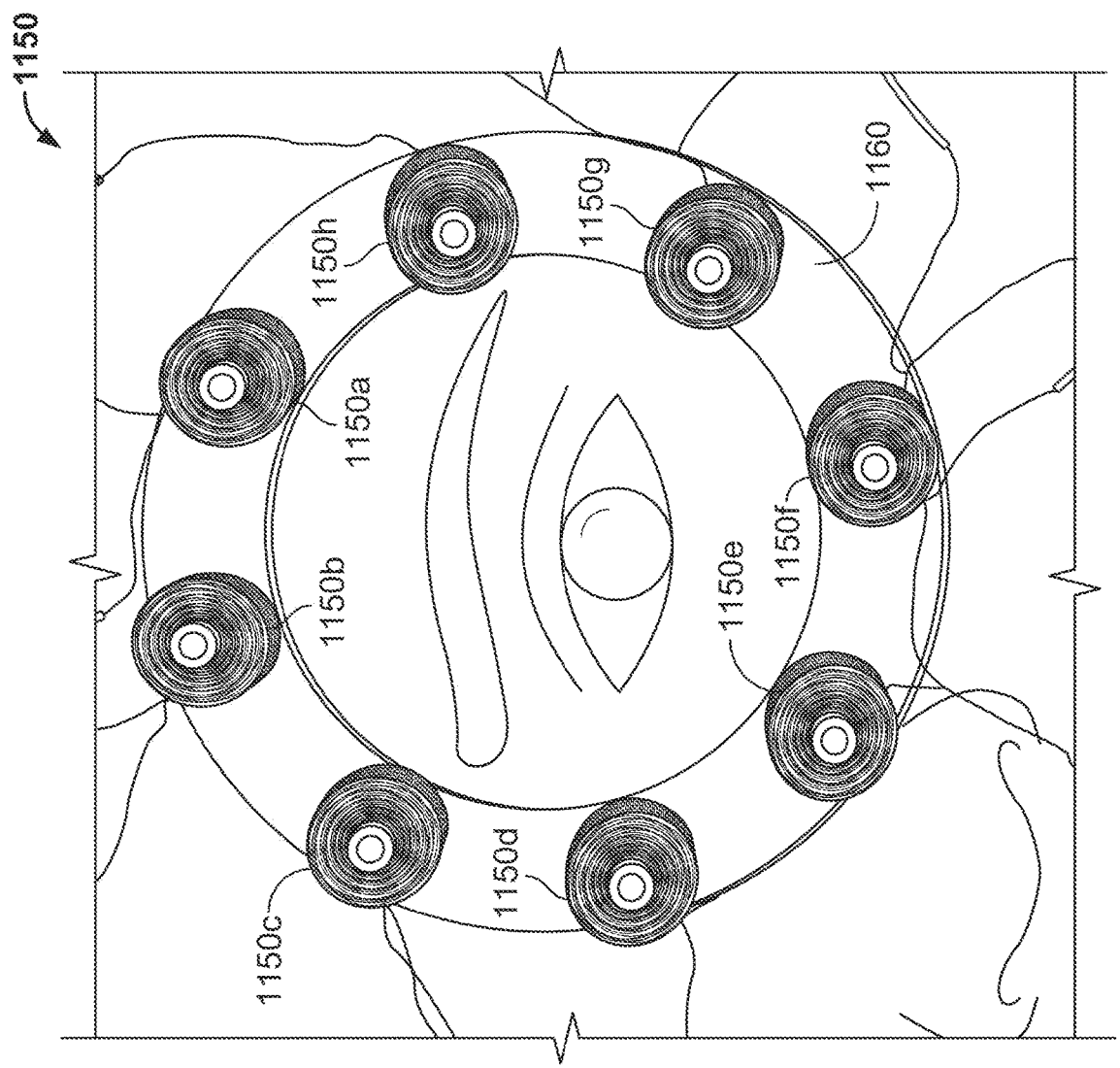

FIGS. 12A-12B illustrate the multi-coil WPT assembly 1150 with each of the coils 1150a-1150h wound individually and soldered together (vs. a single, continuous wire 1154 shown in FIG. 11) and disposed on a base 1160. The base 1160 is generally circular and flat in construction, which allows the coils 1150a-1150h to be mounted thereon (e.g. via glue or other fixation methodologies). Once so constructed, the base 1160 may be mounted to or within any article or structure suitable to position the coils 1150a-1150h close enough to the eye of a mammalian subject such that, in use, the pulsed magnetic fields from the coils 1150a-1150h will create radial current vectors (from the adjacent rotating eddy currents) acting upon the tissues of interest (e.g. ciliary body, Canal of Schlemm) at a therapeutically effective level to reduce the IOP within the eye by decreasing the inflow and/or increasing the outflow of aqueous humor into and out of, respectively, the anterior segment of the eye. By way of example only, the base 1160 may be mounted to or within glasses (e.g. FIGS. 8 and 10) for every-day use, optical frames (e.g. FIG. 9) for clinical use, sleep masks (e.g. FIG. 15) and pillows (e.g. FIG. 16) for night-time use.

Figure 13:
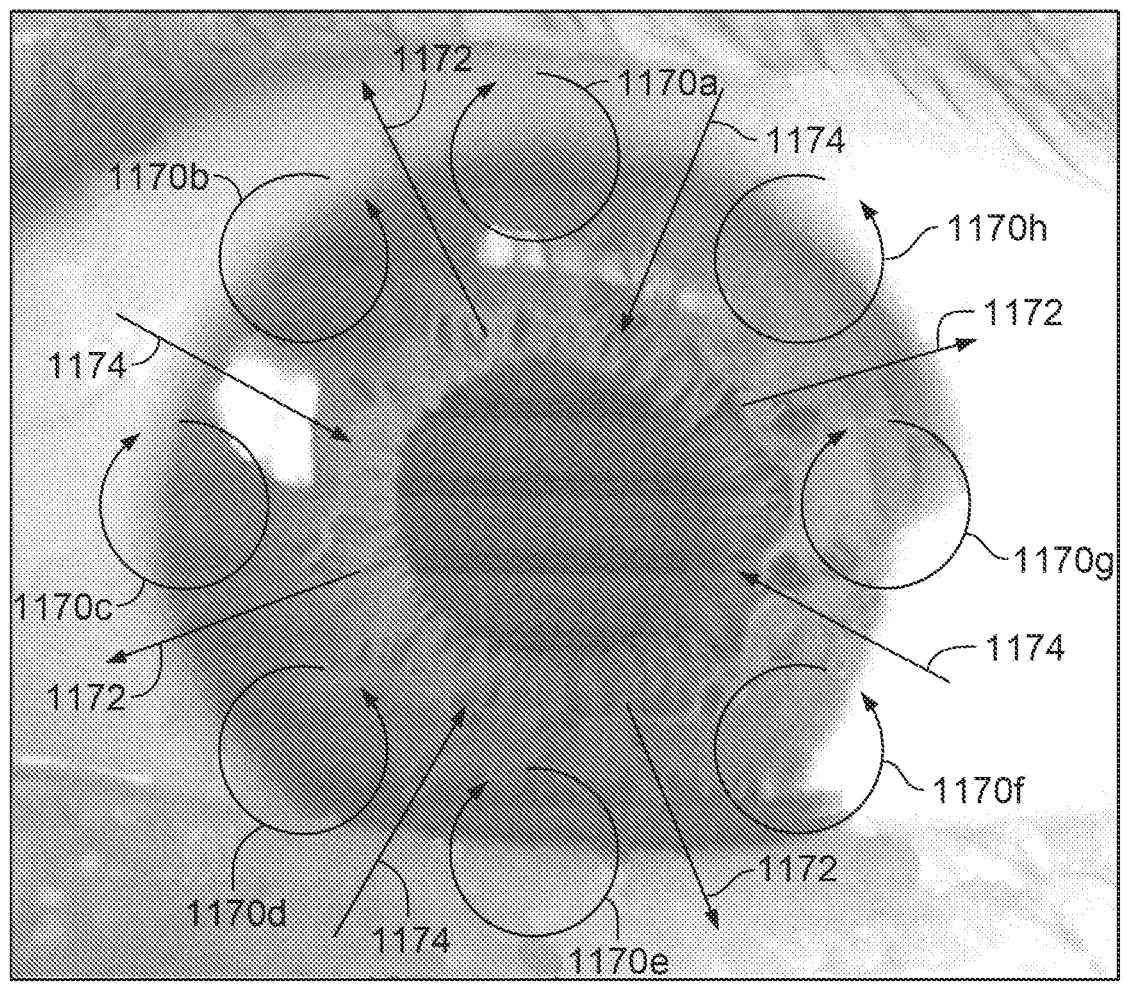
FIG. 13 shows a front perspective view of the currents generated within the eye of a mammalian subject during the operation of the WPT coil assembly of FIG. 10, according to an exemplary embodiment.

FIG. 13 shows a front perspective view of the currents generated within the eye of a mammalian subject during the operation of the WPT coil assembly 1150. Due to the alternating winding directions of the coils 1150a-1150h (e.g. coils 1150a, 1150c, 1150e, 1150g clockwise, and coils 1150b, 1150d, 1150f, 1150h counter-clockwise), a corresponding number of eddy currents are created within the eye with the same alternating directions as the corresponding coil 1150a-1150h. More specifically, eddy current 1170a (clockwise) corresponds to coil 1150a, eddy current 1170b (counter-clockwise) corresponds to coil 1150b, eddy current 1170c (clockwise) corresponds to coil 1150c, eddy current 1170d (counter-clockwise) corresponds to coil 1150d, eddy current 1170e (clockwise) corresponds to coil 1150e, eddy current 1170f (counter-clockwise) corresponds to coil 1150f, eddy current 1170g (clockwise) corresponds to coil 1150g, and eddy current 1170h (counter-clockwise) corresponds to coil 1150h. The rotating eddy currents are induced at the point of impact on the eye surface and create a series of radially outward current vectors 1172 and radially inward current vectors 1174. The radial current vectors 1172, 1174 are configured to pass through structures of interest within the eye of the mammalian subject, including (but not necessarily limited to) the ciliary body and/or Canal of Schlemm. By stimulating these structures of interest, the radial current vectors serve to reduce the IOP within the eye by decreasing the inflow and/or increasing the outflow of aqueous humor into and out of, respectively, the anterior segment of the eye.

Figure 14:
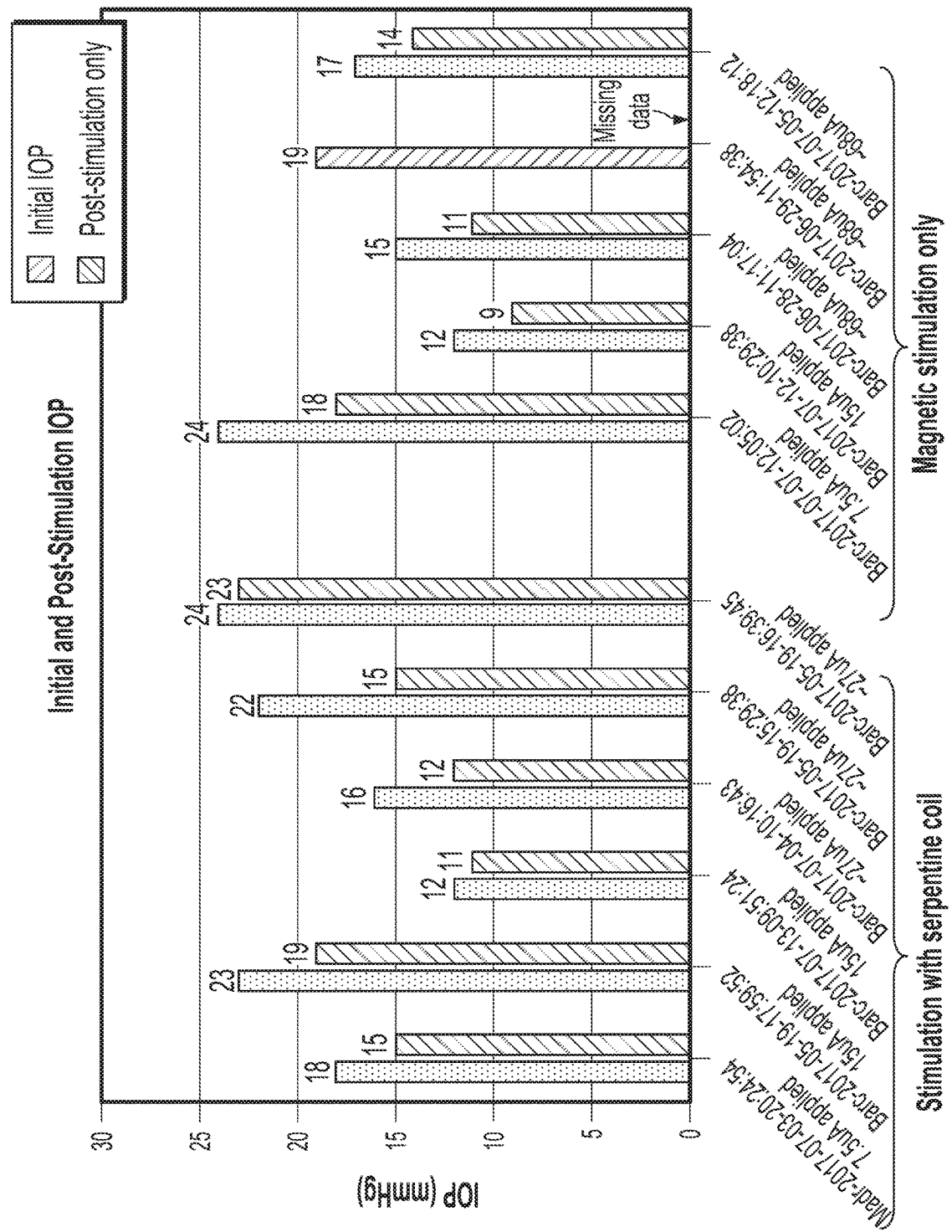
FIG. 14 shows a chart demonstrating the ability of the WPT coil assembly of FIG. 10 to reduce IOP during use with a mammalian subject, according to an exemplary embodiment.

FIG. 14 is a chart demonstrating the results of testing the ability of the multi-coil WPT assembly 1150 to reduce IOP during use with mammalian subjects. The left side of the chart entitled "Stimulation with Serpentine Coil" represents the use of the multi-coil WPT assembly 1150 along with a stimulation coil disposed within a contact lens placed over the eye of the mammalian subject. More specifically, each pair of adjacent bars forming this side of the chart includes a measurement of IOP before testing (left bar) and a measurement of IOP after the administration of pulsed magnetic fields to the stimulation coil on the contact lens of the mammalian subject (right bar). The right side of the chart entitled "Magnetic Stimulation Only" represents the use of the multi-coil WPT assembly 1150 by itself (that is, without a stimulation coil disposed within a contact lens placed over the eye of the mammalian subject). More specifically, each pair of adjacent bars forming this side of the chart includes a measurement of IOP before testing (left bar) and a measurement of IOP after the administration of pulsed magnetic fields to the coils 1150a-1150h while positioned proximate to the eye of the mammalian subject (right bar). It will be readily appreciated that the post-stimulation levels (right bars) are lower than the pre-stimulation levels (left bars), demonstrating that the wireless application of energy of the eye of the mammalian subject according to the principles and techniques disclosed herein does, in fact, result in a reduction of IOP.

Figure 15:
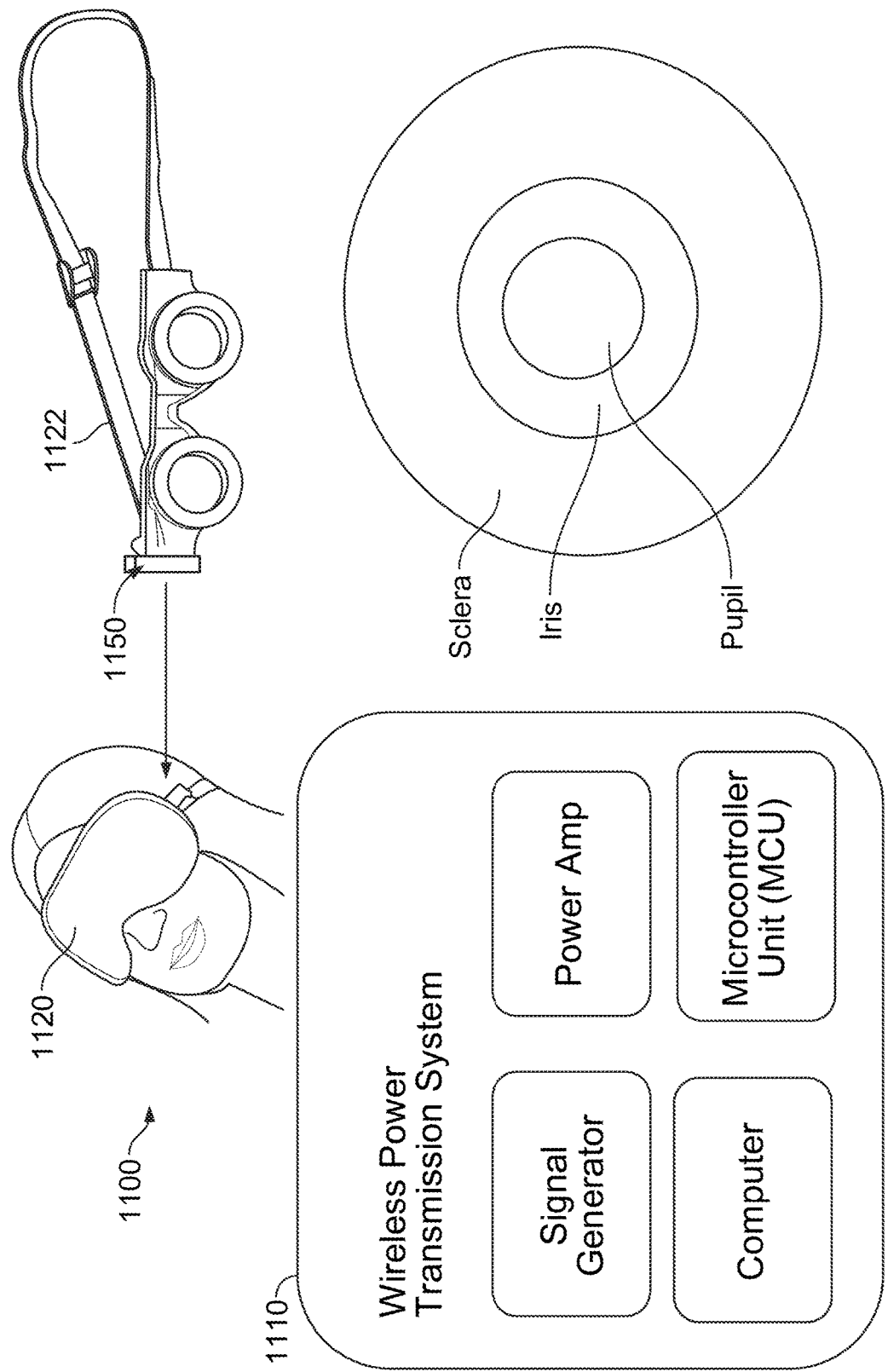
FIG. 15 shows an example wireless glaucoma therapy system involving the use of a wireless power transfer (WPT) coil associated with a sleep mask for implementing the disclosed techniques, according to an exemplary embodiment.

FIG. 15 shows an example wireless glaucoma therapy system 1100 involving the use of a wireless power transfer (WPT) coil associated with a sleep mask for implementing the disclosed techniques. The wireless glaucoma therapy system 1100 is similar in all respects to the prior versions disclosed and described with reference to FIG. 8-12, with the exception that the multi-coil WPT assembly 1150 are dimensioned to be disposed within the sleep mask 1120 (versus part of a pair of glasses or an optical frame). More specifically, the multi-coil WPT assembly 1150 (of the type shown in FIGS. 12A-12B, for example) may be contained within a sleep mask cover 1120, which is equipped with an elastic band 1122 to secure the sleep mask over a user's eyes. By placing the multi-coil WPT assembly 1150 within the fabric cover 1120, a patient may place the individual coils 1150a-1150h adjacent to their eyes over night or during periods of rest where the patient wants to have their eyes closed or light blocked out. This, in turn, allows the patient to continue to receive wireless glaucoma therapy during periods such as overnight, when it wearing glasses is not desirable or comfortable for the patient. Depending upon the amount of wireless glaucoma therapy that needs to be administered over time in order to stave off blindness or the onset of glaucoma, allowing a user to obtain wireless glaucoma therapy night may be an easy way to increase adoption of wireless glaucoma therapy.

Figure 16:
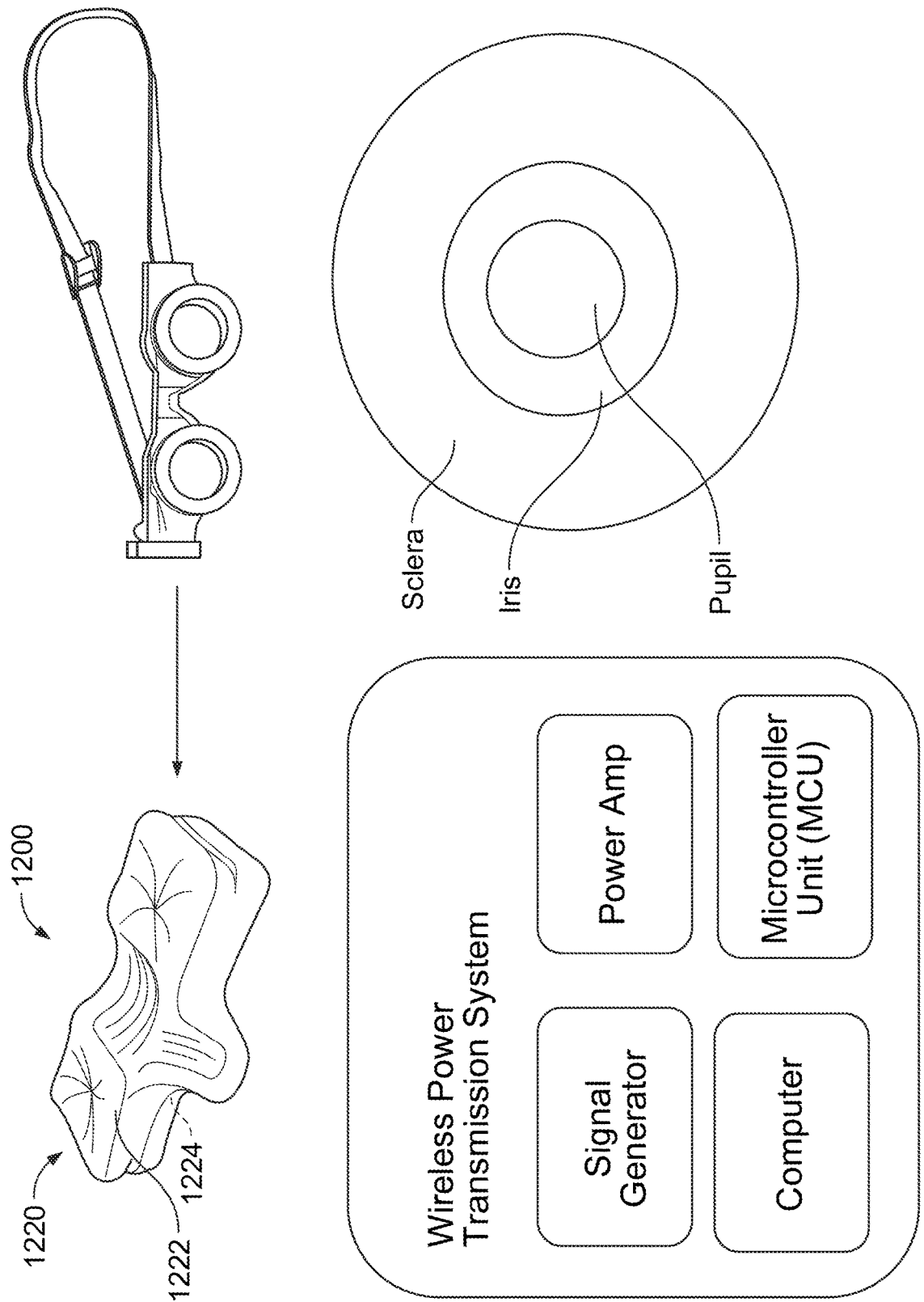
FIG. 16 shows a wireless glaucoma therapy system involving the use of a wireless power transfer (WPT) coil associated with a pillow for implementing the disclosed techniques, according to an exemplary embodiment.

FIG. 16 shows an example of wireless glaucoma therapy system 1200 involving the use of a wireless power transfer (WPT) coil associated with a pillow 1220 for implementing the disclosed techniques. The pillow 1220 can include a soft cover 1222, cushion 1224 disposed within the pillow cover 1222. One or more multi-coil WPT assemblies of the types shown and described herein (e.g. FIGS. 12A-12B) may be disposed within or adjacent to the cushion 1224. The wireless glaucoma therapy system 1200 is similar in all respects to the prior versions disclosed and described with reference to FIG. 8-12, with the exception that the multi-coil WPT assemblies are dimensioned to be disposed within the pillow 1220 (vs. part of a pair of glasses or an optical frame). By placing the multi-coil WPT assemblies within the pillow 1220, a patient may position their head on the pillow 1220 so as to receive wireless glaucoma therapy during periods such as overnight, when wearing glasses is not desirable or comfortable for the patient. Depending upon the amount of wireless glaucoma therapy that needs to be administered over time in order to stave off blindness or the onset of glaucoma, allowing a user to obtain wireless glaucoma therapy night may be an easy way to increase adoption of wireless glaucoma therapy.

Any of the features disclosed and discussed with respect to the manners of positioning multi-coil WPT assemblies in proximity to the eye of FIGS. 8-12 may be combined amongst those shown in the drawings, e.g., features associated with the glasses (FIGS. 8 and 10), optical frames (FIG. 9), sleep mask (FIG. 15) and pillow (FIG. 16).

The various embodiments set forth herein may use different reference numerals throughout the drawings and specification when referring to the same or similar components, features and functionality in other or prior embodiments. Notwithstanding those differences in numbering, it will be appreciated that the disclosures of the various embodiments may be incorporated into the disclosures of the same or similar embodiments so as to facilitate the understanding and appreciation of the many features, functions and inventive aspects within this disclosure.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented using one or more modules of computer program instructions encoded on a computer-readable medium for execution by, or to control the operation of, data processing apparatus. The computer-readable medium can be a manufactured product, such as hard drive in a computer system or an optical disc sold through retail channels, or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM (Erasable Programmable Read-Only Memory), EEPROM (Electrically Erasable Programmable Read-Only Memory), and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., LCD (liquid crystal display), OLED (organic light emitting diode) or other monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The computing system can include clients and servers. A client and server are generally remote from each other and typically interact through a communication network. The relationship of client and server arises by virtue of computer programs running on the respective computers and having a client-server relationship to each other. Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described is this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the disclosure have been described. Other embodiments are within the scope of the following claims. In addition, the actions recited in the claims can be performed in a different order and still achieve desirable results.

What is claimed is:

1. A system for wirelessly controlling intraocular pressure comprising:
    a support structure configured to be positioned external to a surface of an eye of a subject;
    an electrode assembly positioned on the support structure, the electrode assembly comprising a plurality of electrodes configured to control intraocular pressure within the eye, wherein:
        each electrode constructed from an elongated conductor formed into a plurality of windings and configured to be placed in proximity of the eye of the subject and external to a surface of the eye when the support structure is in position,
        the plurality of electrodes comprises a first electrode with a first winding direction and a second electrode with a second winding direction, and
        the first winding direction is different from the second winding direction; and
    a signal generator electrically coupled to the electrode assembly, the signal generator being configured to generate a stimulation signal to produce an electromagnetic field transmitted wirelessly from the electrode assembly to control intraocular pressure within the eye, wherein:
        transmission of the electromagnetic field from the first electrode induces a first eddy current in proximity of the eye,
        transmission of the electromagnetic field from the second electrode induces a second eddy current in proximity of the eye, and
        the first eddy current is different from the second eddy current.

2. The system of claim 1, wherein:
    the plurality of electrodes are arranged in a ring; and
    a center of the ring is adapted to be aligned with a center of a cornea of the eye of the subject.

3. The system of claim 2, wherein the signal generator is configured to reduce an intraocular pressure of the subject by generating the stimulation signal to stimulate at least one intraocular structure in the eye of the subject with at least one electrode of the electrode assembly.

4. The system of claim 1, further comprising a sensor in wireless communication with the signal generator, the signal generator configured to receive a signal from the sensor, the signal representative of a parameter detected at the eye of the subject.

5. The system of claim 4, wherein the signal generator is configured to modify the stimulation signal to produce an electromagnetic field at one or more of the plurality of electrodes of the electrode assembly based on the signal received from the sensor.

6. The system of claim 5, wherein the signal generator is configured to control the stimulation signal to produce an electromagnetic field at one or more of the electrodes of the electrode assembly to create radial current vectors through structures within the eye of the subject.

7. The system of claim 4, wherein the signal generator is configured to generate the stimulation signal to cease generation of the electromagnetic field when the signal received from the sensor exceeds a threshold.

8. The system of claim 4, further comprising a base system in communication with the signal generator, wherein the base system is configured to receive patient data and signal generation data from the signal generator, and wherein the patient data includes the signal representative of the parameter detected by the sensor at the eye of the subject.

9. The system of claim 4, wherein the sensor comprises a pressure sensor.

10. The system of claim 1, wherein:
    the signal generator is configured to receive control signals from a mobile device; and
    the signal generator is configured to be in wireless communication with the mobile device, the control signals being configured to control parameters of the stimulation signal to produce the electromagnetic field.

11. The system of claim 10, wherein:
the parameters comprises at least one of pulse width, current amplitude, and duty cycle.

12. The system of claim 1, wherein the plurality of electrodes of the electrode assembly are formed as coils, and each pair of adjacent coils comprises a first coil having a winding in a first direction and a second coil having a winding in a second direction.

13. The system of claim 12, wherein each pair of adjacent coils of the electrode assembly are configured to produce eddy currents within the eye with alternating directions.

14. The system of claim 1, wherein the support structure comprises an optical frame comprising:
two arms for securing on ears of the subject;
a frame extending between the two arms and defining a viewing aperture; and
wherein the electrode assembly is mounted on the frame and positioned to surround the viewing aperture.

15. The system of claim 1, wherein the support structure comprises a lens configured to be positioned on the surface of the eye of the subject, wherein the electrode assembly is formed as a ring and is positioned with a center of the ring aligned with a center of the lens.

16. A system for controlling intraocular pressure at an eye of a subject, the system comprising:
a support structure configured to be positioned external to a surface of the eye of the subject, at least a portion of the support structure configured to be positioned on an external surface of an eyelid of the subject;
an electrode assembly positioned on the support structure, the electrode assembly comprising a plurality of electrodes arranged in pairs, wherein:
each electrode constructed from an elongated conductor formed into a plurality of windings and configured to be positioned at the external surface of the eyelid of the subject when the support structure is in position,
the plurality of electrodes comprises a first electrode with a first winding direction and a second electrode with a second winding direction, and
the first winding direction is different from the second winding direction; and
a signal generator electrically coupled to the electrode assembly, the signal generator being configured to generate a stimulation signal to produce an electromagnetic field transmitted from the electrode assembly through the eyelid of the subject to control intraocular pressure within the eye, wherein:
transmission of the electromagnetic field from the first electrode induces a first eddy current in proximity of the eye,
transmission of the electromagnetic field from the second electrode induces a second eddy current in proximity of the eye, and
the first eddy current is different from the second eddy current.

17. The system of claim 16, wherein the support structure comprises an eye mask including a cover and a securement mechanism, the securement mechanism being configured to hold the eye mask in position over the eye of the subject.

18. The system of claim 17, wherein:
the plurality of electrodes is arranged in a ring; and
a center of the ring is adapted to be positioned on the eye mask to align with a center of a cornea of the eye of the subject when the eye mask is in position over the eye of the subject.

19. The system of claim 18, wherein the signal generator is configured to reduce an intraocular pressure of the eye of the subject by generating the stimulation signal to stimulate at least one intraocular structure in the eye of the subject with at least one electrode of the electrode assembly to create radial current vectors through structures within the eye of the subject.

20. The system of claim 16, wherein the support structure comprises a pillow configured so as to position the electrode assembly in proximity to the eye when the pillow is placed over the eye of the subject or adjacent to the eye of the subject.

21. A system for wirelessly controlling intraocular pressure comprising:
a support structure configured to be positioned external to a surface of an eye of a subject, the support structure comprising:
an eye mask including a cover; and
a securement mechanism, the securement mechanism being configured to hold the eye mask in position over the eye of the subject, at least a portion of the eye mask cover configured to be positioned on an external surface of an eyelid of a subject when the eye mask is in position over the eye of subject;
an electrode assembly positioned on the support structure, the electrode assembly comprising one or more pairs of electrodes, wherein:
each electrode is constructed from an elongated conductor formed into a plurality of windings and configured to be positioned at the external surface of the eyelid of the subject when the support structure is in position,
each of the one or more pairs of electrodes comprises a first electrode with a first winding direction and a second electrode with a second winding direction, wherein the first winding direction is different from the second winding direction; and
adjacent electrodes are configured to create eddy currents within the eye with alternating directions to control intraocular pressure within the eye; and
a signal generator electrically coupled to the electrode assembly, the signal generator being configured to generate a stimulation signal to produce an electromagnetic field transmitted wirelessly from the electrode assembly to control intraocular pressure within the eye, wherein:
transmission of the electromagnetic field from the first electrode induces a first eddy current in proximity of the eye,
transmission of the electromagnetic field from the second electrode induces a second eddy current in proximity of the eye, and
the first eddy current is different from the second eddy current.

* * * * *